(12) United States Patent
Chenvainu et al.

(10) Patent No.: US 8,444,416 B2
(45) Date of Patent: May 21, 2013

(54) VALVES FOR PERSONAL CARE DEVICES

(75) Inventors: Alexander T. Chenvainu, Sudbury, MA (US); Thomas A. Christman, Lexington, MA (US); Manfred Klawuhn, Frankfurt am Main (DE)

(73) Assignee: Braun GmbH, Kronberg (DE)

( * ) Notice: Subject to any disclaimer, the term of this patent is extended or adjusted under 35 U.S.C. 154(b) by 1434 days.

(21) Appl. No.: 11/114,987

(22) Filed: Apr. 26, 2005

(65) Prior Publication Data

US 2006/0240380 A1    Oct. 26, 2006

(51) Int. Cl.
*A61C 17/00* (2006.01)
*A46B 9/04* (2006.01)

(52) U.S. Cl.
USPC ............................................. 433/80; 15/167.1

(58) Field of Classification Search
USPC ..................... 137/512.15, 846, 849; 433/80; 132/112–116; 15/167.1
See application file for complete search history.

(56) References Cited

U.S. PATENT DOCUMENTS

| | | |
|---|---|---|
| 1,327,757 A | 1/1920 | Eggers |
| 1,664,369 A | 3/1928 | Maurer |
| 2,303,667 A | 12/1942 | Taborski |
| 2,661,537 A | 12/1953 | Angell |
| 2,691,553 A | 10/1954 | Pettigrew |
| 2,696,049 A | 12/1954 | Black |
| 2,757,688 A | 8/1956 | Meyer-Saladin |
| 2,759,266 A | 8/1956 | Cassani |
| 2,813,529 A | 11/1957 | Ikse |
| 3,134,127 A | 5/1964 | Klein |
| 3,164,153 A | 1/1965 | Zorzi |
| 3,195,537 A * | 7/1965 | Blasi .............................. 601/114 |
| 3,234,953 A | 2/1966 | Moynihan |
| 2,743,042 A | 4/1966 | Burgin |
| 3,334,646 A | 8/1967 | Billeter et al. |
| 3,400,996 A | 9/1968 | Macrum |
| RE26,589 E | 5/1969 | Murov |
| 3,445,916 A | 5/1969 | Schulte |
| D214,829 S | 8/1969 | Muscatiello |
| 3,496,933 A | 2/1970 | Lloyd |
| 3,504,699 A | 4/1970 | Grisé |
| 3,536,065 A | 10/1970 | Moret |
| 3,578,887 A | 5/1971 | Turolla |
| 3,593,707 A | 7/1971 | Pifer |
| 3,608,548 A | 9/1971 | Lewis |

(Continued)

FOREIGN PATENT DOCUMENTS

| | | |
|---|---|---|
| CA | 1151 821 | 8/1983 |
| DE | 238191 | 11/1910 |

(Continued)

OTHER PUBLICATIONS

International Search Report in connection with PCT/US2006/015392, mailed on Feb. 12, 2007, 5 pages.

(Continued)

*Primary Examiner* — Heidi M Eide
(74) *Attorney, Agent, or Firm* — John P. Colbert; Vladimir Vittenberg; James C. Vago

(57) ABSTRACT

Dual valves are described herein. The dual valves have a plurality of lumens disposed within a unitary body. The dual valves can be used, for example, in personal care products such as toothbrushes and razors to dispense fluids such as dentifrice and shaving aids.

20 Claims, 19 Drawing Sheets

U.S. PATENT DOCUMENTS

| | | |
|---|---|---|
| 3,610,514 A | 10/1971 | Samsing |
| 3,628,875 A | 12/1971 | Wild |
| 3,771,186 A | 11/1973 | Moret |
| 3,823,710 A | 7/1974 | Borden |
| 3,864,047 A | 2/1975 | Sherrod |
| 3,870,039 A | 3/1975 | Moret |
| 3,878,577 A | 4/1975 | Jousson |
| 3,903,888 A | 9/1975 | Buelow et al. |
| 3,910,706 A | 10/1975 | Del Bon |
| 3,971,136 A | 7/1976 | Madsen |
| 3,972,123 A | 8/1976 | Black |
| 4,109,836 A | 8/1978 | Falarde ......................... 222/494 |
| 4,146,020 A | 3/1979 | Moret |
| 4,155,663 A | 5/1979 | Cerquozzi |
| 4,174,571 A | 11/1979 | Gallant |
| 4,178,975 A | 12/1979 | Crespi |
| 4,201,200 A | 5/1980 | Hubner |
| 4,214,871 A | 7/1980 | Arnold |
| 4,222,126 A | 9/1980 | Boretos et al. ...................... 3/1.5 |
| 4,236,889 A | 12/1980 | Wright |
| 4,322,207 A | 3/1982 | Madsen |
| 4,412,402 A | 11/1983 | Gallant |
| 4,422,450 A | 12/1983 | Rusteberg |
| 4,429,434 A | 2/1984 | Sung Shan |
| 4,434,810 A | 3/1984 | Atkinson |
| 4,467,822 A | 8/1984 | Blackwell |
| 4,518,557 A | 5/1985 | Wecker |
| 4,522,597 A | 6/1985 | Gallant |
| 4,524,805 A | 6/1985 | Hoffman ....................... 137/846 |
| 4,534,340 A | 8/1985 | Kerr |
| 4,540,365 A | 9/1985 | Nelson |
| 4,583,563 A | 4/1986 | Turner |
| 4,595,365 A | 6/1986 | Edel |
| 4,619,009 A * | 10/1986 | Rosenstatter ....................... 15/29 |
| 4,691,623 A | 9/1987 | Mizusawa ...................... 98/2.18 |
| 4,692,047 A | 9/1987 | Endo |
| 4,696,644 A | 9/1987 | Goof |
| 4,735,200 A | 4/1988 | Westerman |
| 4,743,199 A | 5/1988 | Weber |
| 4,770,632 A | 9/1988 | Ryder |
| 4,776,794 A | 10/1988 | Meller |
| 4,818,191 A | 4/1989 | Schlake |
| 4,863,302 A | 9/1989 | Herzfeld |
| 4,903,688 A | 2/1990 | Bibby |
| 4,906,187 A | 3/1990 | Amadera |
| 4,941,459 A | 7/1990 | Mathur |
| 4,950,160 A | 8/1990 | Karst |
| 4,963,046 A | 10/1990 | Eguchi |
| 5,055,043 A | 10/1991 | Weiss |
| 5,062,795 A | 11/1991 | Woog |
| 5,066,155 A | 11/1991 | English |
| 5,098,291 A | 3/1992 | Curtis |
| 5,113,585 A | 5/1992 | Rogers et al. ...................... 30/41 |
| 5,120,219 A | 6/1992 | De Farcy |
| 5,142,723 A | 9/1992 | Lustig |
| 5,147,203 A | 9/1992 | Seidenberg |
| 5,189,751 A | 3/1993 | Giuliani et al. ................ 15/22.1 |
| 5,203,698 A | 4/1993 | Blake |
| 5,208,933 A | 5/1993 | Lustig |
| 5,219,274 A | 6/1993 | Pawlowski |
| 5,261,459 A | 11/1993 | Atkinson et al. .............. 137/846 |
| 5,286,192 A | 2/1994 | Dixon |
| 5,301,381 A | 4/1994 | Klupt |
| 5,321,866 A | 6/1994 | Klupt |
| 5,332,370 A | 7/1994 | Nakayama |
| 5,338,124 A | 8/1994 | Spicer |
| 5,344,317 A | 9/1994 | Pacher |
| 5,346,324 A | 9/1994 | Kuo |
| 5,387,182 A | 2/1995 | Otani |
| 5,393,153 A | 2/1995 | Bouthillier |
| 2,709,546 A | 5/1995 | Shore |
| 5,411,491 A | 5/1995 | Goldhardt et al. ............. 604/247 |
| 5,454,164 A | 10/1995 | Yin et al. ......................... 30/41 |
| 5,454,896 A | 10/1995 | Harding et al. |
| 5,474,544 A | 12/1995 | Lynn |
| 5,484,281 A * | 1/1996 | Renow et al. .................... 433/80 |
| 5,492,147 A | 2/1996 | Challender et al. |
| 5,501,426 A | 3/1996 | Atkinson et al. |
| 5,503,553 A | 4/1996 | Hines |
| 5,509,433 A | 4/1996 | Paradis |
| 5,524,312 A | 6/1996 | Tan et al. |
| 5,530,215 A | 6/1996 | Couvreur |
| 5,540,358 A | 7/1996 | Wiles et al. |
| 5,573,398 A | 11/1996 | Towle |
| 5,578,059 A | 11/1996 | Patzer |
| 5,593,304 A | 1/1997 | Ram |
| 5,600,933 A | 2/1997 | Wiles et al. |
| 5,653,591 A | 8/1997 | Loge |
| 5,690,017 A | 11/1997 | Riedlinger |
| 5,699,821 A | 12/1997 | Paradis |
| 5,702,033 A * | 12/1997 | Beaver ........................... 222/94 |
| 5,711,488 A | 1/1998 | Lund |
| 5,730,336 A | 3/1998 | Lerner ......................... 222/490 |
| 5,746,595 A | 5/1998 | Ford |
| 5,755,572 A | 5/1998 | Bab et al. |
| 5,769,585 A | 6/1998 | Pudolsky |
| 5,806,831 A | 9/1998 | Paradis |
| 5,820,373 A | 10/1998 | Okano |
| 5,871,353 A * | 2/1999 | Pierce et al. .................... 433/84 |
| 5,909,977 A | 6/1999 | Kuo |
| 5,918,995 A | 7/1999 | Puurunen |
| 5,921,692 A | 7/1999 | Weber |
| 5,974,613 A | 11/1999 | Herzog |
| 6,030,215 A | 2/2000 | Ellion |
| 6,039,301 A | 3/2000 | Westerhof |
| 6,039,302 A | 3/2000 | Cote et al. |
| 6,065,389 A | 5/2000 | Riedlinger |
| 6,068,011 A | 5/2000 | Paradis |
| 6,079,432 A | 6/2000 | Paradis |
| 6,092,551 A | 7/2000 | Bennett ......................... 137/846 |
| 6,106,288 A | 8/2000 | Brassil |
| 6,113,068 A | 9/2000 | Ryan |
| 6,136,253 A | 10/2000 | Bennett ...................... 264/328.1 |
| 6,164,967 A | 12/2000 | Sale |
| 6,189,859 B1 | 2/2001 | Rohrbough et al. |
| 6,217,327 B1 | 4/2001 | Bedi |
| 6,220,772 B1 | 4/2001 | Taylor |
| 6,233,773 B1 | 5/2001 | Karge |
| 6,241,412 B1 | 6/2001 | Spies et al. |
| 6,264,119 B1 | 7/2001 | Truong |
| 6,299,443 B1 | 10/2001 | Gerstner |
| 6,315,483 B1 | 11/2001 | Velliquette |
| 6,331,088 B2 | 12/2001 | Owens |
| 6,347,614 B1 | 2/2002 | Evers |
| 6,357,125 B1 | 3/2002 | Feldmann et al. |
| 6,371,674 B1 | 4/2002 | Lerner |
| 6,375,459 B1 | 4/2002 | Kamen |
| 6,382,255 B2 | 5/2002 | McFarland .................... 137/849 |
| 6,402,410 B1 | 6/2002 | Hall et al. |
| 6,419,485 B1 | 7/2002 | Pond |
| 6,434,773 B1 | 8/2002 | Kuo |
| 6,457,476 B1 * | 10/2002 | Elmer et al. ................... 132/114 |
| 6,536,979 B1 | 3/2003 | Kenny |
| 6,564,972 B2 * | 5/2003 | Sawhney et al. .............. 222/137 |
| 6,574,820 B1 | 6/2003 | DePuydt et al. |
| 6,575,203 B2 | 6/2003 | Hall et al. |
| 6,602,071 B1 | 8/2003 | Ellion |
| 6,644,878 B2 | 11/2003 | Hall et al. |
| 6,648,641 B1 * | 11/2003 | Viltro et al. ..................... 433/80 |
| 6,681,803 B2 | 1/2004 | Taneya et al. |
| 6,702,255 B2 | 3/2004 | Dehdashtian .............. 251/149.3 |
| 6,745,998 B2 | 6/2004 | Doyle |
| 6,766,549 B2 | 7/2004 | Klupt |
| 6,766,824 B2 | 7/2004 | Taylor |
| 6,808,161 B1 | 10/2004 | Hishikawa |
| 6,808,331 B2 | 10/2004 | Hall |
| 6,883,778 B1 | 4/2005 | Newton et al. |
| 6,884,069 B2 | 4/2005 | Goldman |
| 6,902,337 B1 | 6/2005 | Kuo |
| 6,957,925 B1 * | 10/2005 | Jacobs et al. ................... 401/270 |
| 7,036,179 B1 * | 5/2006 | Weihrauch ................... 15/167.1 |
| 7,080,980 B2 | 7/2006 | Klupt |
| 7,147,468 B2 | 12/2006 | Snyder et al. |
| 7,161,489 B2 | 1/2007 | Sullivan |
| 7,341,208 B2 | 3/2008 | Peters et al. |
| 7,469,440 B2 | 12/2008 | Boland et al. |
| 7,530,796 B2 | 5/2009 | Yu et al. |

| | | | | | | |
|---|---|---|---|---|---|---|
| 2001/0054448 | A1 | 12/2001 | McFarland ............... 137/849 | DE | 20306197 | 7/2003 |
| 2003/0027100 | A1 | 2/2003 | Grant | DE | 102007025485.2 | 5/2007 |
| 2003/0033680 | A1 | 2/2003 | Davies et al. | EP | 1107453 | 6/2001 |
| 2003/0060743 | A1 | 3/2003 | Chang | FR | 1193546 | 11/1959 |
| 2003/0086745 | A1 | 5/2003 | Micaletti | FR | 1491238 | 7/1967 |
| 2003/0099502 | A1 | 5/2003 | Lai | GB | 233018 | 4/1925 |
| 2003/0126705 | A1 | 7/2003 | Hanlon | GB | 762230 | 11/1956 |
| 2003/0150472 | A1 | 8/2003 | Johnson | GB | 2019961 | 11/1979 |
| 2003/0152565 | A1 | 8/2003 | Bartorelli | GB | 2087025 | 5/1982 |
| 2003/0194678 | A1 | 10/2003 | Viltro et al. | GB | 2343619 A | 5/2000 |
| 2004/0047676 | A1 | 3/2004 | Dumler | GB | 2378894 | 2/2003 |
| 2004/0057773 | A1 | 3/2004 | Gray | JP | 63286147 | 11/1988 |
| 2004/0126331 | A1 | 7/2004 | Corcoran et al. | JP | 9215524 | 8/1997 |
| 2004/0131560 | A1 | 7/2004 | Corcoran et al. | JP | 10033571 | 4/1998 |
| 2004/0141799 | A1 | 7/2004 | Jackow | WO | WO 82/00576 | 3/1982 |
| 2004/0143917 | A1 | 7/2004 | Ek | WO | WO 95/08934 A1 | 4/1995 |
| 2004/0150258 | A1 | 8/2004 | McCarthy | WO | WO 99/23975 | 5/1999 |
| 2005/0000541 | A1 | 1/2005 | Engel | WO | WO 00/45731 | 8/2000 |
| 2005/0004498 | A1* | 1/2005 | Klupt ............... 433/80 | WO | WO 00/74592 | 12/2000 |
| 2005/0060822 | A1 | 3/2005 | Chenvainu | WO | WO 01/03542 A2 | 1/2001 |
| 2005/0158688 | A1 | 7/2005 | Tarr | WO | WO 03/063643 A1 | 8/2003 |
| 2005/0271531 | A1 | 12/2005 | Christman et al. | WO | WO 2005/058186 A1 | 6/2005 |
| 2005/0272001 | A1 | 12/2005 | Blain et al. | WO | WO2006/067748 | 6/2006 |
| 2005/0272002 | A1 | 12/2005 | Chenvainu et al. | WO | WO2006/067760 | 6/2006 |
| 2005/0281758 | A1 | 12/2005 | Dodd | WO | WO2008/145320 | 12/2008 |
| 2006/0078844 | A1 | 4/2006 | Cohen et al. | WO | WO2008/155025 | 12/2008 |
| 2006/0159509 | A1 | 7/2006 | Grez et al. | | | |
| 2006/0188454 | A1 | 8/2006 | Corcoran et al. | | | |
| 2006/0193792 | A1 | 8/2006 | Corcoran et al. | | | |
| 2006/0240380 | A1 | 10/2006 | Chenvainu et al. | | | |
| 2006/0289031 | A1 | 12/2006 | Grez et al. | | | |
| 2007/0017582 | A1 | 1/2007 | Chenvainu et al. | | | |
| 2007/0105065 | A1 | 5/2007 | Snyder et al. | | | |
| 2007/0113903 | A1 | 5/2007 | Black | | | |
| 2007/0212662 | A1 | 9/2007 | Grez | | | |
| 2007/0254260 | A1 | 11/2007 | Alden et al. | | | |
| 2007/0275347 | A1 | 11/2007 | Gruber | | | |
| 2009/0017423 | A1 | 1/2009 | Gottenbos et al. | | | |
| 2009/0070949 | A1 | 3/2009 | Sagel | | | |
| 2009/0085515 | A1 | 4/2009 | Bourilkov | | | |
| 2009/0191071 | A1 | 7/2009 | Yu et al. | | | |

FOREIGN PATENT DOCUMENTS

| | | |
|---|---|---|
| DE | 2041495 | 4/1972 |
| DE | 2343421 | 3/1975 |
| DE | 2758182 | 7/1978 |
| DE | 2746453 C2 | 4/1979 |
| DE | 2819404 | 8/1979 |
| DE | 3904139 | 8/1990 |
| DE | 9107226 | 10/1991 |
| DE | 29816089 | 1/1999 |
| DE | 10137879 | 2/2003 |

OTHER PUBLICATIONS

DWPI Accession No. 2003-240906 (Feb. 20, 2003).
DWPI Accession No. 2003-241468 (Feb. 26, 2003).
DWPI Accession No. 2003-277227 (Feb. 6, 2003).
DWPI Accession No. 2003-468010 (May 29, 2003).
DWPI Accession No. 2003-560479 (2003).
DWPI Accession No. 2003-567147 (2003).
DWPI Accession No. 2003-568454 (2003).
DWPI Accession No. 2003-575803 (2003).
DWPI Accession No. 2003-577960 (2003).
Office Action for U.S. Appl. No. 10/861,086 dated Aug. 14, 2008; Blain et al.; filed Jun. 3, 2004.
Office Action for U.S. Appl. No. 10/861,086 dated Dec. 10, 2007; Blain et al.; filed Jun. 3, 2004.
Office Action for U.S. Appl. No. 10/861,086 dated Jan. 8, 2007; Blain et al.; filed Jun. 3, 2004.
Office Action for U.S. Appl. No. 11/185,480 dated Mar. 13, 2009; Chenvainu et al.; filed Jul. 20, 2005.
Office Action for U.S. Appl. No. 11/185,480 dated Oct. 1, 2008; Chenvainu et al.; filed Jul. 20, 2005.
Office Action for U.S. Appl. No. 11/185,480 dated Dec. 28, 2007; Chenvainu et al.; filed Jul. 20, 2005.

* cited by examiner

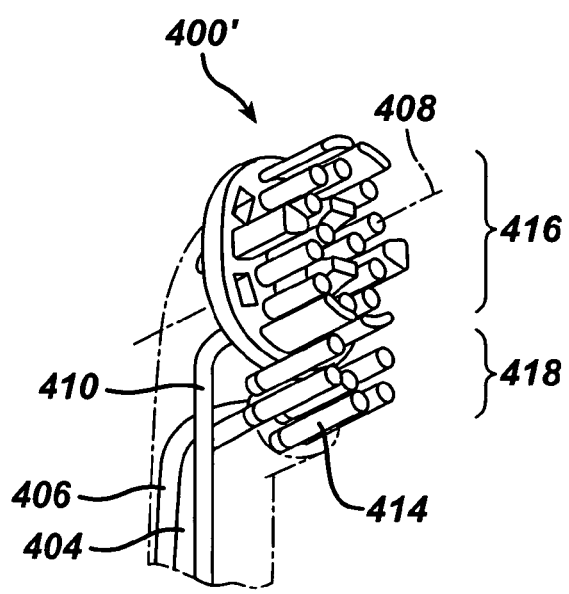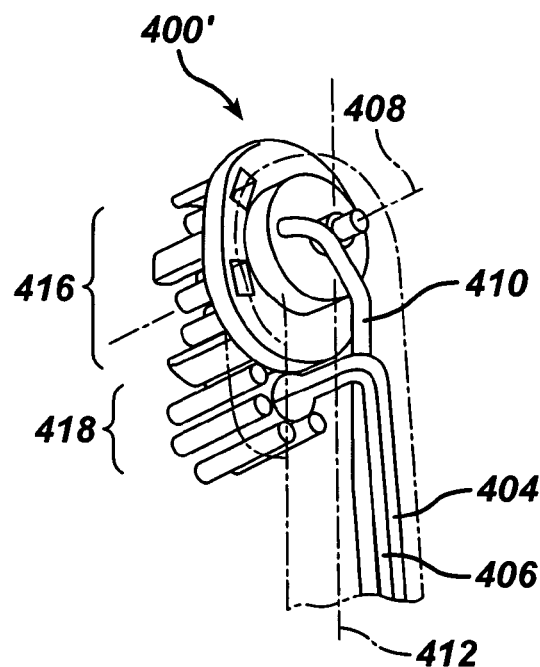
FIG. 11A  FIG. 11B

VALVES FOR PERSONAL CARE DEVICES

TECHNICAL FIELD

This invention relates to valves, and more particularly to valves for personal care devices, e.g., razors and toothbrushes that dispense a plurality of fluids. The invention also relates to personal care devices that include such valves.

BACKGROUND

Small valves have been used to control delivery of a fluid from a personal care device, for example delivery of a dentifrice from a toothbrush or a shaving cream from a razor. It is desirable that such valves be compact, to minimize the space occupied on the personal care device. Examples of dispensing toothbrushes that use such valves are included in U.S. patent application Ser. No. 10/861,253, filed Jun. 3, 2004, the entire contents of which is hereby incorporated by reference.

In some instances a toothbrush or other personal care product dispenses two or more components. For example the two components can chemically react upon contact to produce a cooling sensation or a warming sensation. Therefore, in some instances, it is desirable to ensure that the components remain separate from each other until dispensed, for example in the mouth or on the skin of the user.

SUMMARY

In one aspect, the invention features an oral care device. The device includes: a body, constructed to be held by a user, including two or more passageways through which fluids can flow, and a head, extending from the body and being sized to fit in a user's mouth, the head including an outlet, in fluid communication with the passageways, through which the fluids can be dispensed to the user's mouth, and disposed within the outlet to control fluid flow therefrom, a single, unitary valve body defining a plurality of lumens, each lumen being in fluid communication with one of the passageways and terminating in a valve.

In some embodiments, the oral care device includes one or more of the following features. Each lumen can share a common wall with an adjacent lumen. The oral care device can also include a plurality of bristles extending from said head. The oral care device can also include reservoirs, in communication with the passageways, configured to contain a supply of each of the fluids. The reservoirs can be, for example, disposed within the body, or disposed within a docking station in fluid communication with the body. The valve body can include tapered lumens. The valves can include, for example, slit valves or duckbill valves. The valve body can be substantially cylindrical. The top of the cylinder cam be domed. At least one of the first and second valves can include a sealing means. The valve body can also include ribs positioned transversely to at least one of the valves, wherein the ribs apply force to the valve to close the valve.

At least one of the lumens can taper from a relatively wide cross-sectional area at a proximal end to a relatively narrow cross-sectional area at a distal end. The common wall can extend entirely from the proximal end to the distal end. The common wall can extend partially from the proximal end to the distal end.

At least one valve can include a slit opening. For example, each valve can include a slit opening, where the slit openings are co-linear, or each valve can include a slit opening, where the slit openings are substantially parallel.

At least one lumen can have an elliptical cross-section, a circular cross-section, or a D-shaped cross-section. The lumens can have a cross sectional area of at least about 0.0003 inches$^2$ at the base. The valve body can have a height of between about 0.100 inches and about 0.500 inches. The valve body can include an elastomer. The valve body can dispense media at a rate of between about 0.2 ml/minute and about 6.0ml/minute.

The device can be a toothbrush, for example a power toothbrush or a manual toothbrush. The valve body can be disposed in the center of the head. At least one of the fluids can include a dentifrice. The valve body can be disposed in the center of the head and the plurality of bristles can be disposed surrounding the valve body. The valve body can be disposed within the head and at least 1 tuft of bristles or cleaning element is adjacent to the valve body.

The first lumen can include a first media and the second lumen can include a second media, which is different from the first media. The media dispensed from the first and second lumens can chemically react with each other upon dispensing.

The head can be substantially round, elongated, or substantially elliptical. The head can oscillate. The device can include multiple heads. For example one head can be stationary and one head can move. The valve can be positioned in the stationary head.

In another aspect, the invention features a method of brushing the teeth of a subject. The method includes; inserting into the oral cavity of the subject an oral care device including a body including two or more passageways through which fluids can flow, and a head extending from the body, the head including an outlet, in fluid communication with the passageways, through which the fluids can be dispensed to the user's mouth, and disposed within the outlet to control fluid flow therefrom, a single, unitary valve body defining a plurality of lumens, each lumen being in fluid communication with one of the passageways and terminating in a valve; and brushing the teeth of the subject.

In another aspect, the invention features a razor. The razor includes; a body, constructed to be held by a user, including two or more passageways through which fluids can flow, a head extending from the body, wherein the head includes an outlet in fluid communication with the passageways, through which the fluids can be dispensed to the skin of a user, and a blade unit comprising a housing having a front portion, a rear portion and two side surfaces extending from the front portion to the rear portion, and one or more shaving blades positioned between the front portion and the rear portion; and disposed within the outlet to control fluid flow therefrom, a single, unitary valve body defining a plurality of lumens, each lumen being in fluid communication with one of the passageways and terminating in a valve.

In some embodiments, the razor includes one or more of the following features. The blade unit also includes a guard member. The outlet can be within the guard member. The guard member can also include an opening through which the valve body extends. The guard member can include an elastomeric structure. The blade unit can include three or more blades. The blade unit can also include a cap and, mounted on the cap, a lubricating strip. The outlet can be positioned within the cap. The razor can also include reservoirs, in communication with the passageways, each reservoir being configured to contain a supply of one of the fluids. The valve body can include tapered lumens. The valves can include slit valves or duckbill valves. At least a portion of the valve body can be substantially cylindrical.

In another embodiment, the invention includes a method of shaving. The method includes providing a razor described herein and contacting the razor with skin, for example, skin of a human or other mammal.

In another aspect, the invention includes an oral care device including a head sized and shaped to fit into the mouth of a user, an outlet positioned on the head; and a shearing member rotatably attached proximate the outlet, said shearing member configured to engage a fluid stream exiting the outlet.

In some embodiments, the shearing member includes an inner cylindrical member; and an outer cylindrical member, wherein said outer member includes a plurality openings, and wherein the inner and outer cylindrical members are configured to rotate relative to each other, co-acting to engage the fluid stream to distribute the fluid through the openings. The openings can be, for example, slots extending parallel to an axis of rotation of the cylinder, distributing the fluid through the slots in a radial direction. Or, in some embodiments, the openings can be substantially circular. In some embodiments, the mixing member also includes a cap positioned over the inner and outer cylindrical members. In some embodiments, the shearing member includes openings positioned over the outlet where the fluid passes axially through the openings. The openings can be, for example, circular.

In some embodiments, the shearing member includes a plurality of radially extending elongated members having openings positioned there between.

The shearing member can be formed from, for example, thermoplastic, thermoplastic elastomer, or a combination thereof.

The oral care device can be, for example an electric or a manual toothbrush.

In another aspect, the invention features an oral care device including a head sized and shaped to fit into the mouth of a user, an outlet positioned on the head; and a shearing means rotatably attached proximate the outlet for mixing a fluid exiting the outlet.

In another aspect, the invention features a razor including a body, constructed to be held by a user, including two or more passageways through which fluids can flow, a head, extending from the body, wherein the head includes an outlet in fluid communication with the passageways, through which the fluids can be dispensed to the skin of a user, and a blade unit including a cutting mechanism, said shearing member configured to engage a fluid stream exiting the outlet. The cutting mechanism can include, for example, a housing having a front portion, a rear portion and two side surfaces extending from the front portion to the rear portion, and one or more shaving blades positioned between the front portion and the rear portion; an outlet positioned on the head; and a shearing member rotatably attached proximate the outlet.

In some embodiments, the shearing member includes an inner cylindrical member; and an outer cylindrical member, wherein said outer member includes a plurality openings, and wherein the inner and outer cylindrical members are configured to rotate relative to each other, co-acting to engage the fluid stream to distribute the fluid through the openings. The openings can be, for example, slots extending parallel to an axis of rotation of the cylinder, distributing the fluid through the slots in a radial direction. Or, in some embodiments, the openings can be substantially circular. In some embodiments, the mixing member also includes a cap positioned over the inner and outer cylindrical members. In some embodiments, the shearing member includes openings positioned over the outlet where the fluid passes axially through the openings. The openings can be, for example, circular.

In some embodiments, the shearing member includes a plurality of radially extending elongated members having openings positioned there between.

The shearing member can be formed from, for example, thermoplastic, thermoplastic elastomer, or a combination thereof.

The razor can be, for example an electric or a manual razor.

In another aspect, the invention features a razor including a body, constructed to be held by a user, including two or more passageways through which fluids can flow, a head, extending from the body, wherein the head includes an outlet in fluid communication with the passageways, through which the fluids can be dispensed to the skin of a user, and a blade unit including a cutting mechanism; an outlet positioned on the head; and a shearing means rotatably attached proximate the outlet for mixing a fluid exiting the outlet. The cutting mechanism can include, for example, a housing having a front portion, a rear portion and two side surfaces extending from the front portion to the rear portion, and one or more shaving blades positioned between the front portion and the rear portion.

As used herein, the term "slit valve" refers to an elastomeric valve where the sealing of the valve is provided by a closed slit, and flow is provided by flexing of the elastomer, which causes the slit to open. In general, the slit valve is a single piece construction, which is free of moving parts.

The term "duckbill valve" is a term of art and is used herein as such.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 11A and 11B are front and rear perspective views of the head and neck of another oral care device embodiment.

Like reference symbols in the various drawings indicate like elements.

DETAILED DESCRIPTION

The valves described herein can be used, for example, in hand-held personal care devices such as a toothbrush or a razor. Examples of such personal care devices are described in U.S. patent application Ser. No. 10/861,253,filed Jun. 3, 2004,the complete disclosure of which is incorporated herein by reference.

Figure 1:
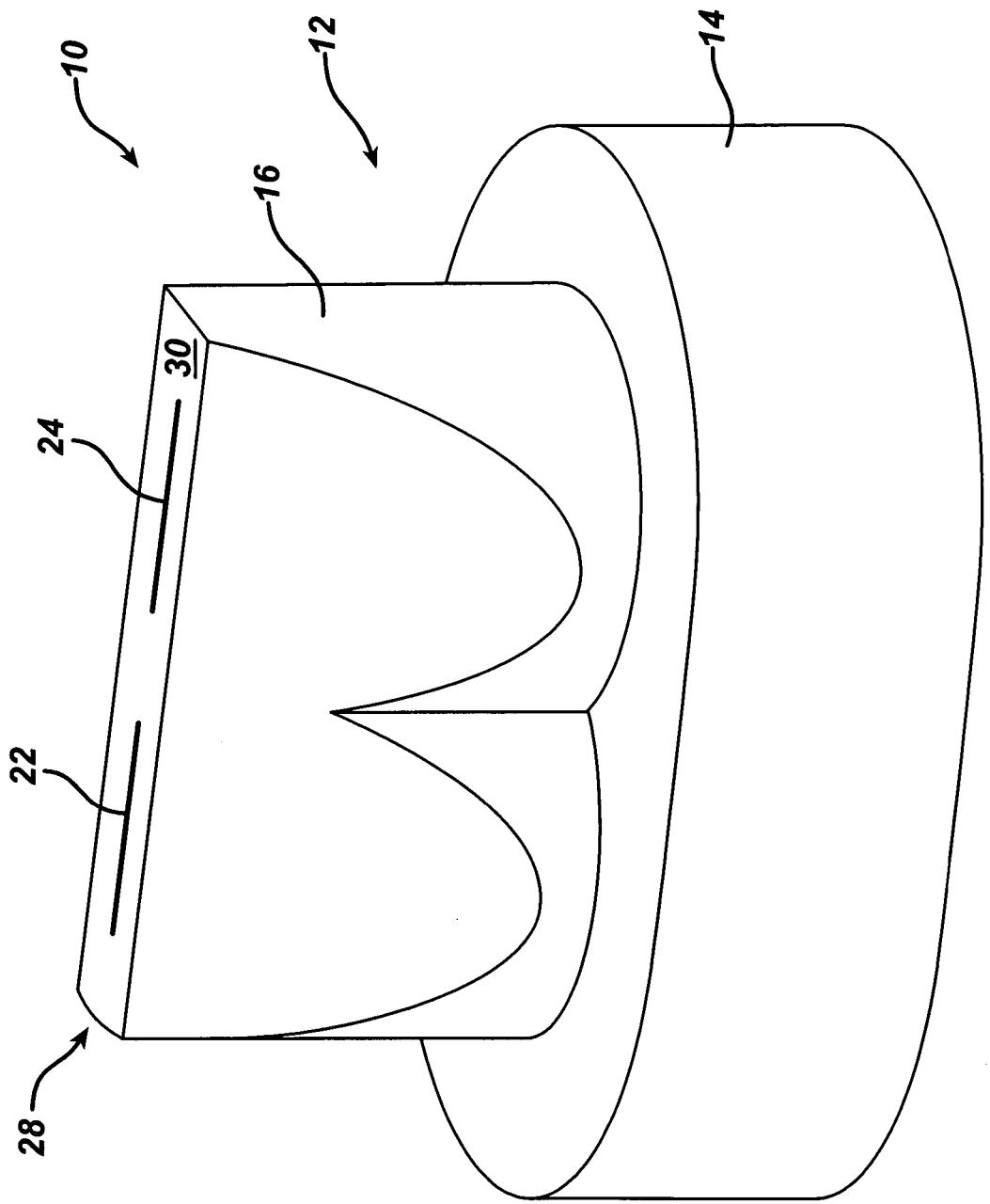
FIG. 1 is a front perspective view of a dual duckbill valve.

Referring to FIG. 1, a dual duckbill valve 10 includes a single unitary body 12 having a base 14 and an upper portion 16. The body 12 defines two lumens 18,20 (FIGS. 2 and 3) through which fluid can pass, each lumen terminating in said valve. The valves are substantially closed; the slits 22,24 open in response to pressure from the fluid inside the lumens. As shown in FIG. 1, the slits 22,24 are positioned co-linearly with respect to each other. In some instances, co-linear slits provide ease in manufacturing, for example, relative to slits that are positioned parallel to each other.

Figure 2:
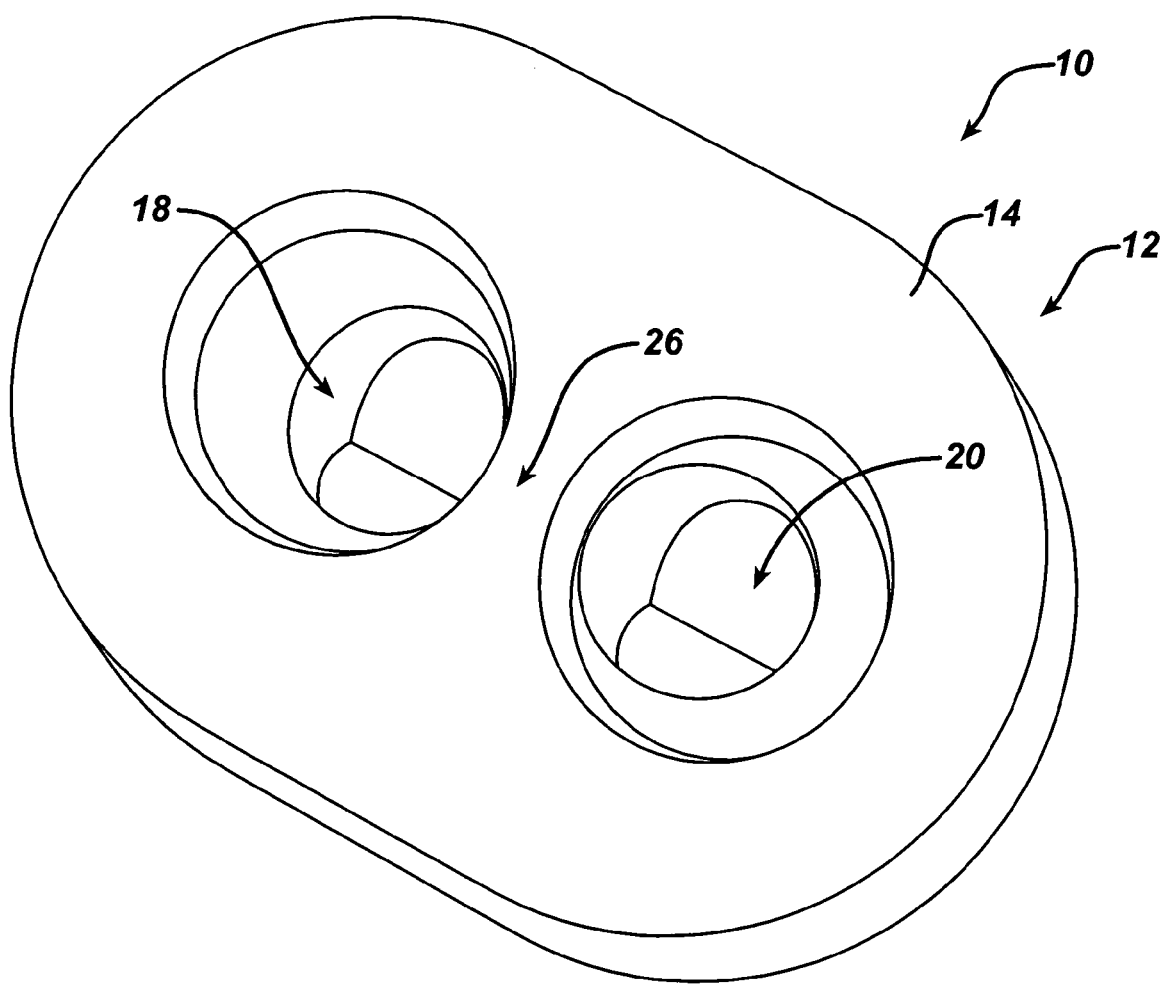
FIG. 2 is a bottom perspective view of the dual duckbill valve of FIG. 1.
Figure 3:
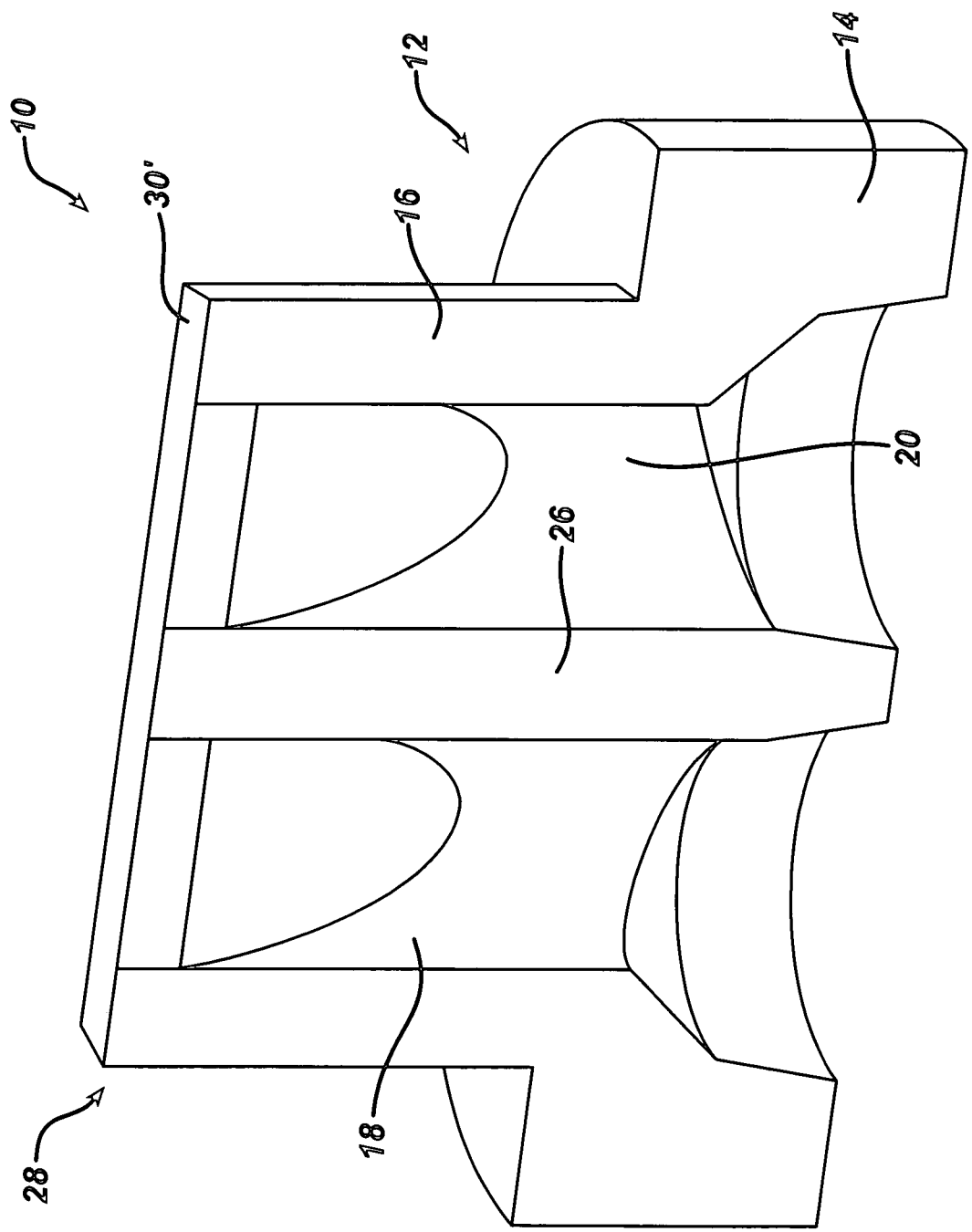
FIG. 3 is a perspective cross-sectional view of the dual duckbill valve of FIG. 1.

Referring to FIGS. 2 and 3, the lumens 18,20 share a common wall 26, which extends entirely from the base 14 to the distal end 28 of the dual duckbill valve. At the base, the lumens are approximately circular in cross-section, whereas at the distal ends, the lumens are approximately rectangular in cross-section. The body 12 is generally elongated when viewed from above, and surface 30' (FIG. 3) at distal end 28 is generally rectangular, with slits 22,24 extending along the length of the rectangle. The base 14 is configured to form a seal with an outlet (or a pair of outlets) in the head of a personal care device such as a toothbrush or a razor, thus allowing the components to flow from the passageways (not shown) into the lumens 18,20 of the valve 10, while preventing undesired fluid communication at the opening(s) of the head on which the valve is positioned. Moreover, the base of the common wall 26 also forms a seal at the head of the device, thus preventing mixing of two components of a composition as the components flow from passageways (not shown) into the lumens of the dual duckbill valve.

Figure 4:
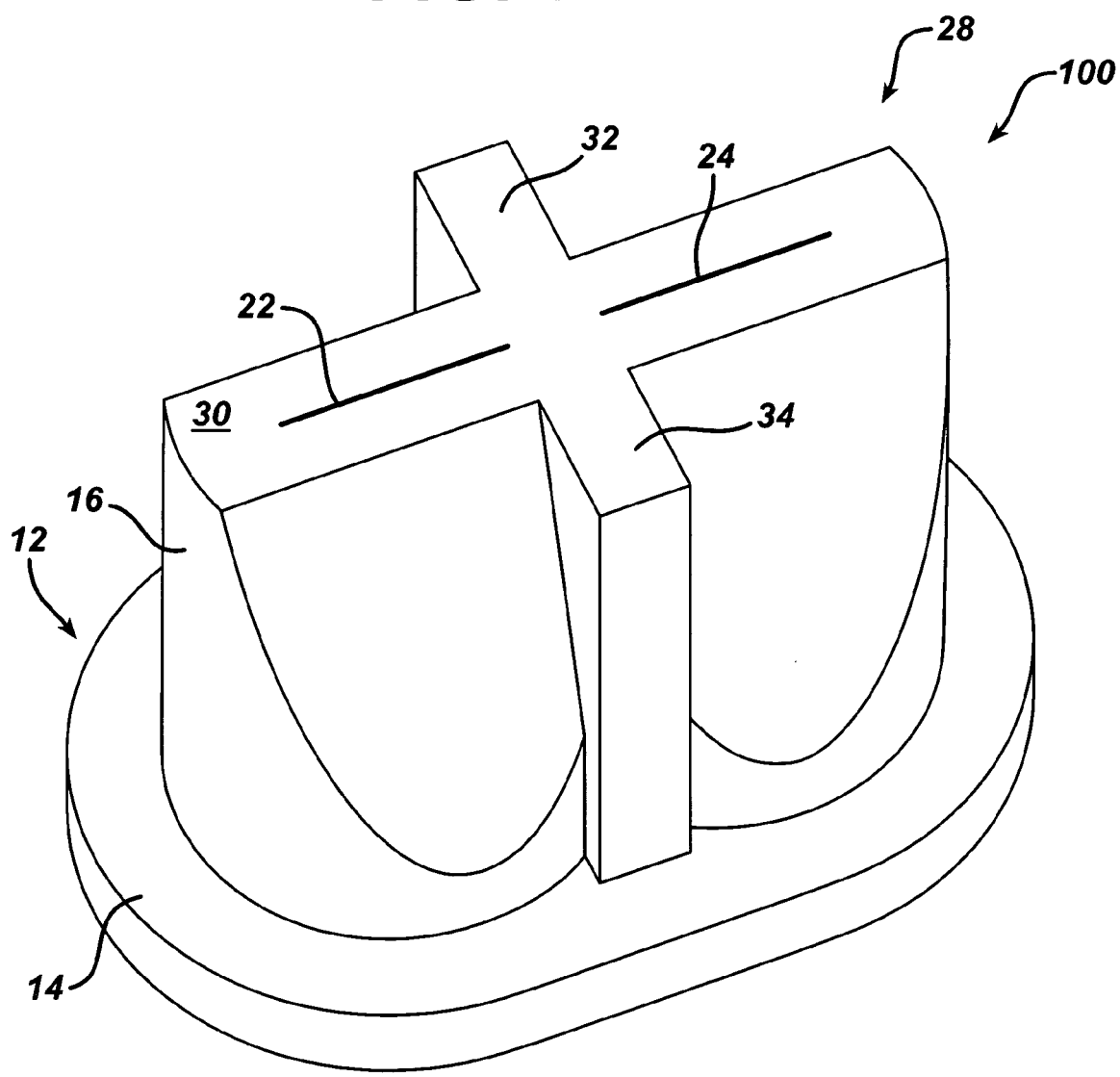
FIG. 4 is a front perspective view of a dual duckbill valve having a set of cross-ribs.

FIG. 4 depicts a dual duckbill valve 100 that includes a set of transverse ribs 32,34 in the center of the unitary body. The ribs are centered between the slits 22,24, and extend generally perpendicular to the slits. The ribs extend the full height of upper portion 16 i.e., from the top portion of the base 14 to the distal end 28 of the unitary body. The ribs do not extend horizontally to overlap with the slits that form the valve on the distal end of the body. The transverse ribs can provide support to the upper portion 16 of the body. In some instances, the ribs can be used to create high shear mixing, for example in combination with the structures shown in FIGS. 15 and 16 below.

Figure 5:
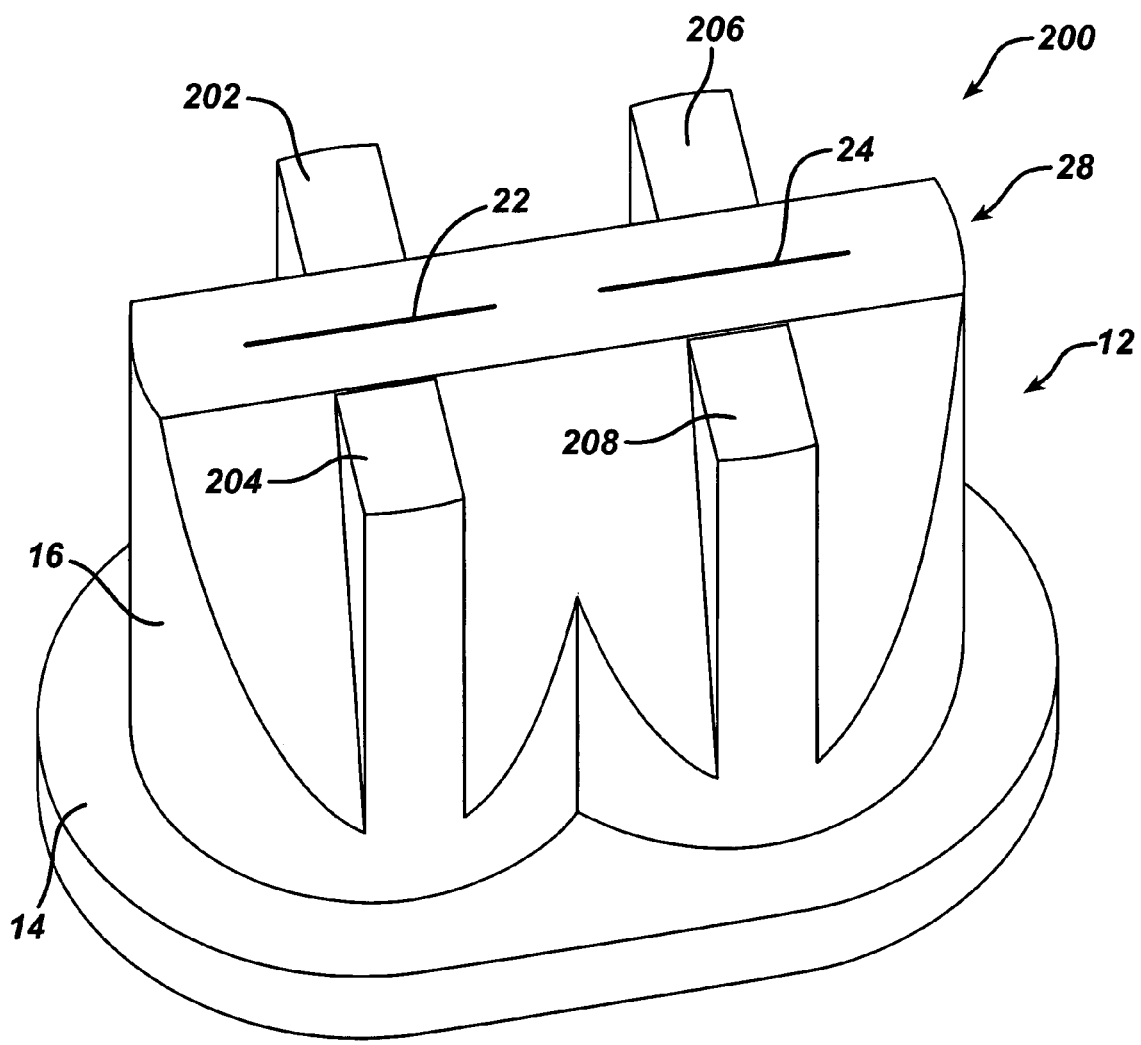
FIG. 5 is a front perspective view of a dual duckbill valve having two sets of cross-ribs.

FIG. 5 depicts a dual duckbill valve 200 that includes two sets of transverse ribs 202,204 and 206,208. The ribs extend vertically in the manner discussed above, but each set of transverse ribs is centered horizontally one of the slits 22,24 at the distal end 28 of the body 12. Positioned in this manner, the ribs can provide pressure on the slit opening to remain closed, thus preventing leakage from the valve opening. As noted above, the ribs can also be used to generate high shear mixing. Examples of a single lumen valve including ribs are disclosed in U.S. Pat. No. 4,434,810,the entire contents of which is hereby incorporated by reference.

Figure 6:
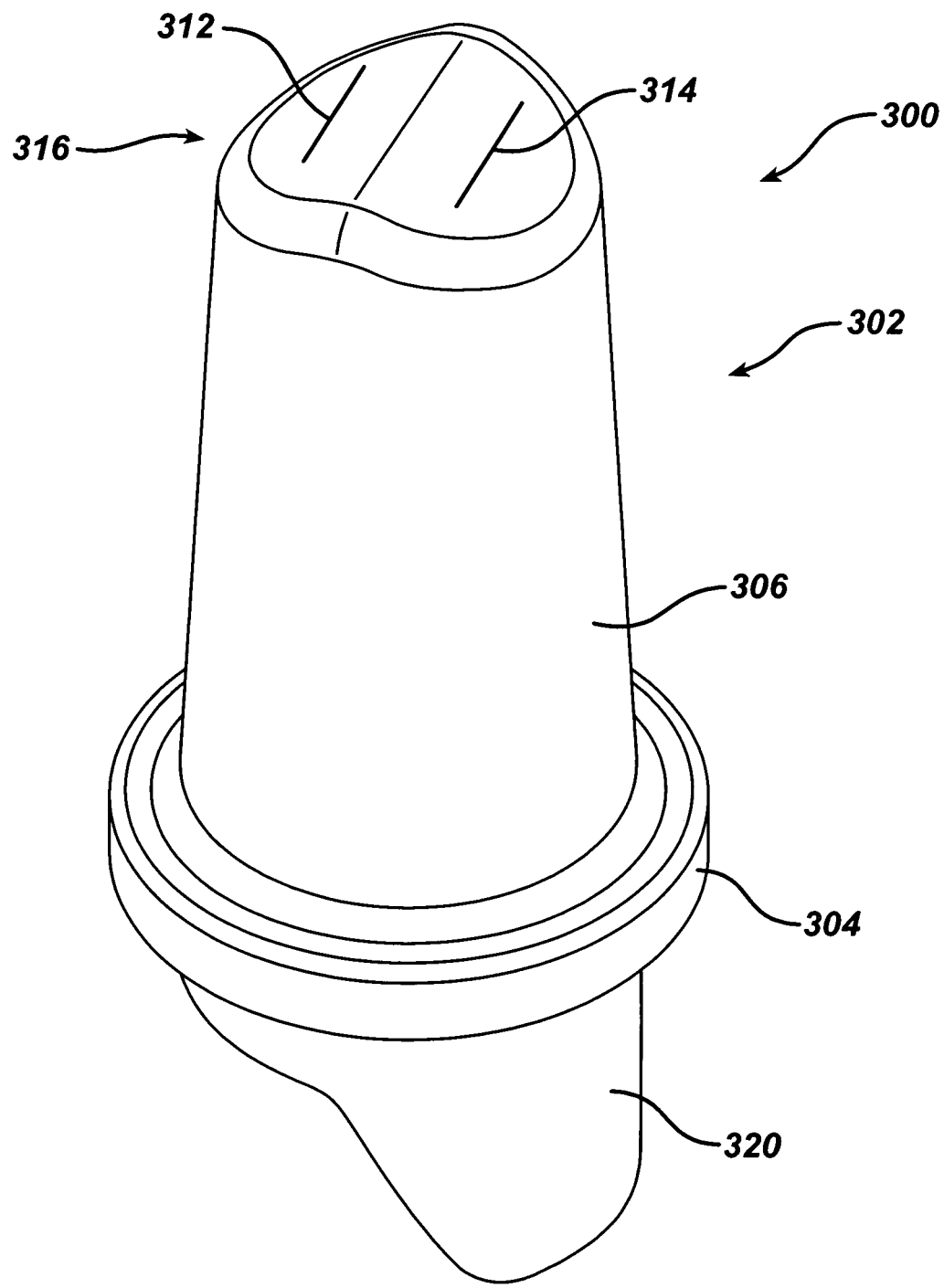
FIG. 6 is a front perspective view of a dual valve.

FIG. 6 depicts a dual valve 300 having a single unitary body 302 including a base 304, an upper portion 306, a lower portion 320, and two lumens 308, 310 (FIGS. 7 and 8) through which fluid can pass, each lumen terminating in a slit valve 312,314 at distal end 316. A portion of the lumens extends below the base into the lower portion 320 that can be positioned within a personal care device such as a toothbrush or a razor. In this embodiment, the slit valves are positioned parallel relative to each other. In some instances, the parallel positioning of the slit valves provides an overall circular shape of the dual valve. The circular shape can be a preferable shape to accommodate the rotating and/or oscillating motion of the head of an oral care device.

Figure 7:
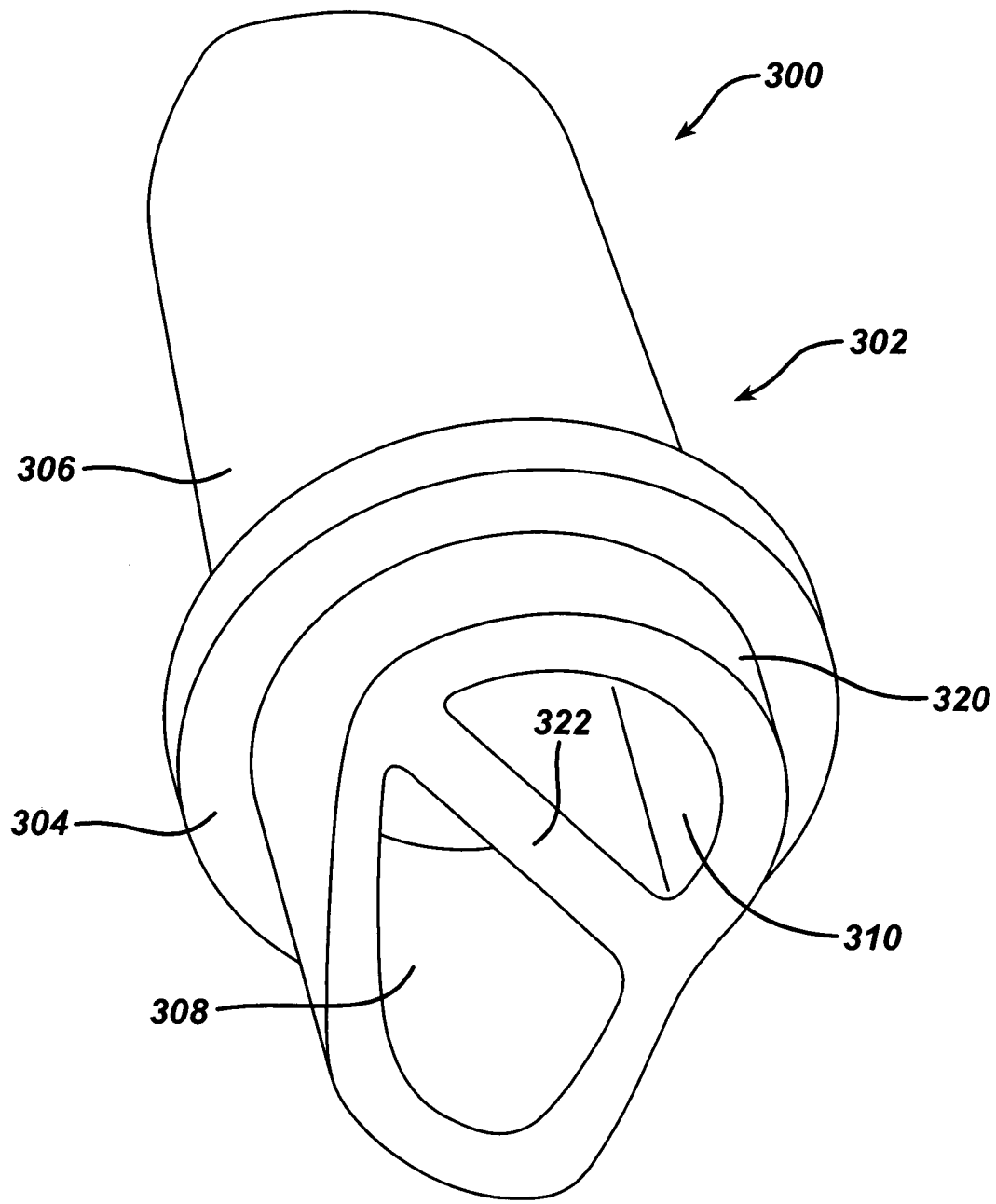
FIG. 7 is a bottom perspective view of the dual valve of FIG. 6.
Figure 8:
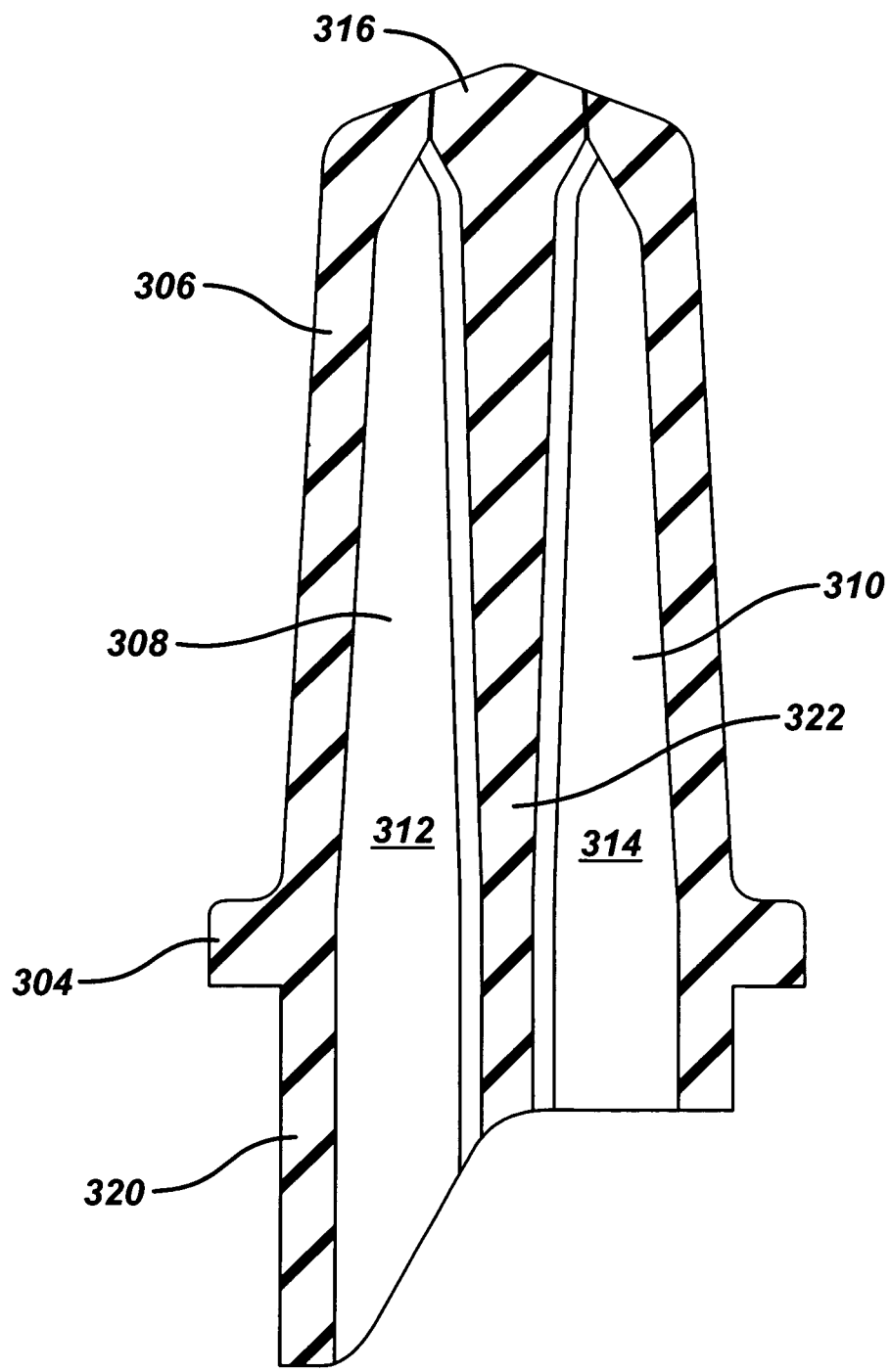
FIG. 8 is a cross-sectional view of the dual valve of FIG. 6.

Referring to FIGS. 7 and 8, the lumens 308,310 share a common wall 322 and are approximately D-shaped in cross section. As the lumens extend from the lower portion 320 to the distal ends, the cross-sectional area of each lumen decreases. The lumens are configured to provide a unitary body that is approximately circular in cross-section, thus providing an efficient use of space when positioned within a personal care product. The distal end of the unitary body is raised in the middle portion. In some instances, the distal end of the unitary body is flat.

Figure 9:
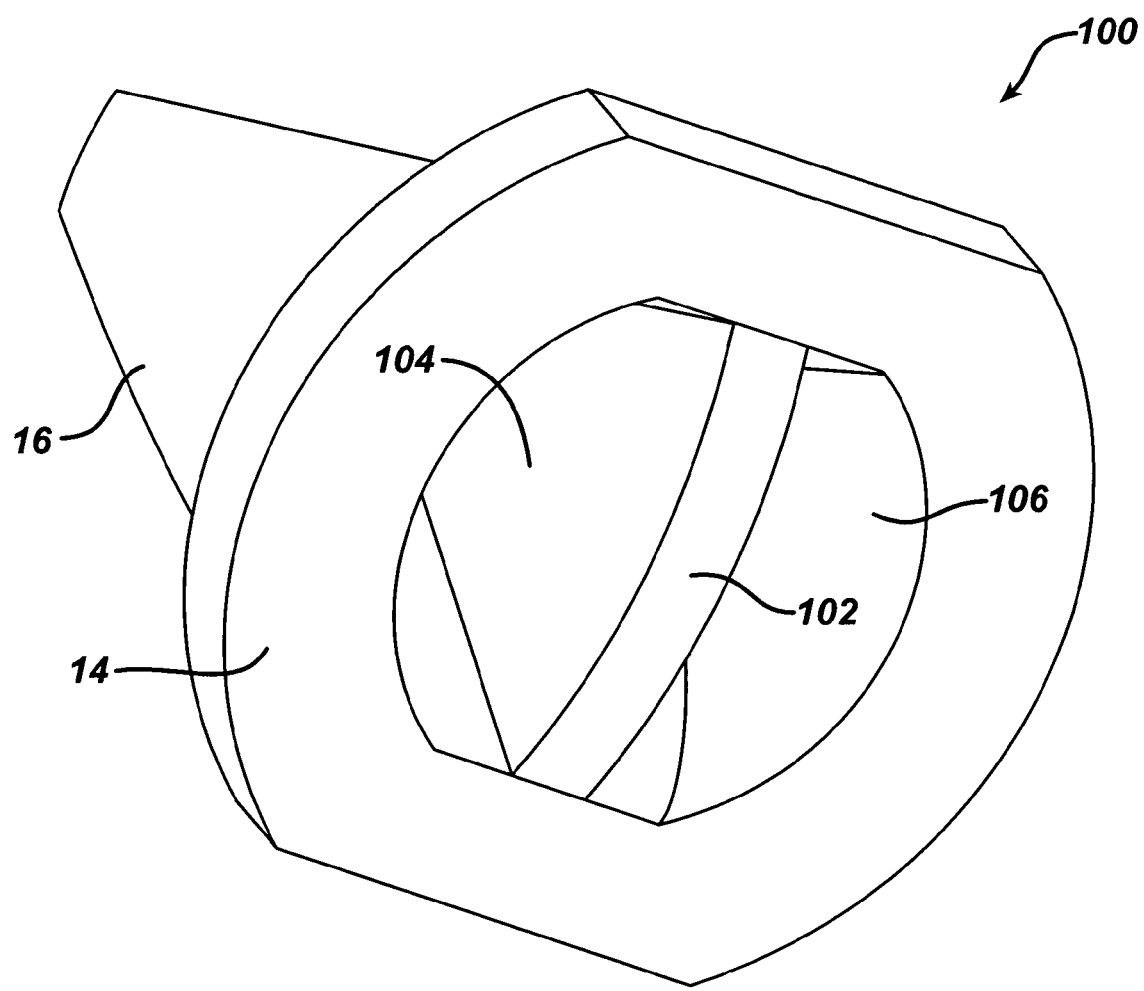
FIG. 9 is a bottom perspective view of a dual duckbill valve.

As can be seen in FIG. 9, the lumens 104,106 of the duckbill valve 100 share a common wall 102. In this instance, the common wall extends substantially from the distal end to the base of the unitary structure such that the common wall has a slight arcuate shape at the base of the unitary structure. The arcuate structure extends below the base 14 and is compressed with the head of the device when the valve is positioned and sealed onto the head. The compression of the common wall 102 onto the head provides a mechanism of preventing fluid communication between the two passageways (not shown) as the components flow from the passageways into the two lumens 104,106 having a D-shaped cross-section.

Toothbrushes

Figure 10:
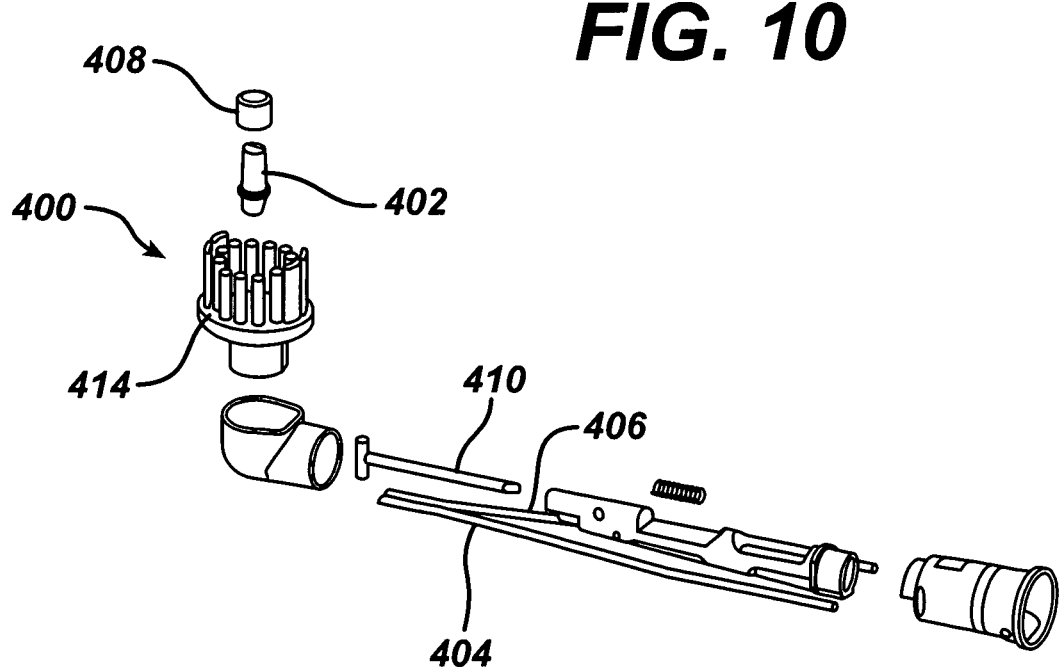
FIG. 10 is a top perspective view of the head and neck of another oral care device embodiment.

The valves described herein can be used in personal care products, including but not limited to toothbrushes and razors. These products can be used, for example, in a manual or a powered device (e.g., an electric toothbrush or razor). Referring to FIG. 10, a movable head 400 includes a valve 402. In this embodiment, a valve 402 and associated fluid passageways 404,406 extend through a rotatable head 400. A drive shaft 410 is connected to the rotatable head 400. Cleaning elements 414 are positioned on the movable head 400, surrounding the valve 402. A prophy cup 408 is positioned over valve, surrounding valve and providing a means to capture the fluid as it passes through the valve. As another example, referring to FIGS. 11A and 11B, a head 400' having a longitudinal axis 412 includes a movable portion 416 and a stationary portion 418 with a valve 402 and associated fluid passageways 404,406 positioned in the stationary portion 418. As an alternative, the valve 402 can be positioned within the movable portion 416, rather than in the stationary portion 418. The movable portion 416 can be formed by a rotatable head that is connected to a drive shaft.

Figure 12:
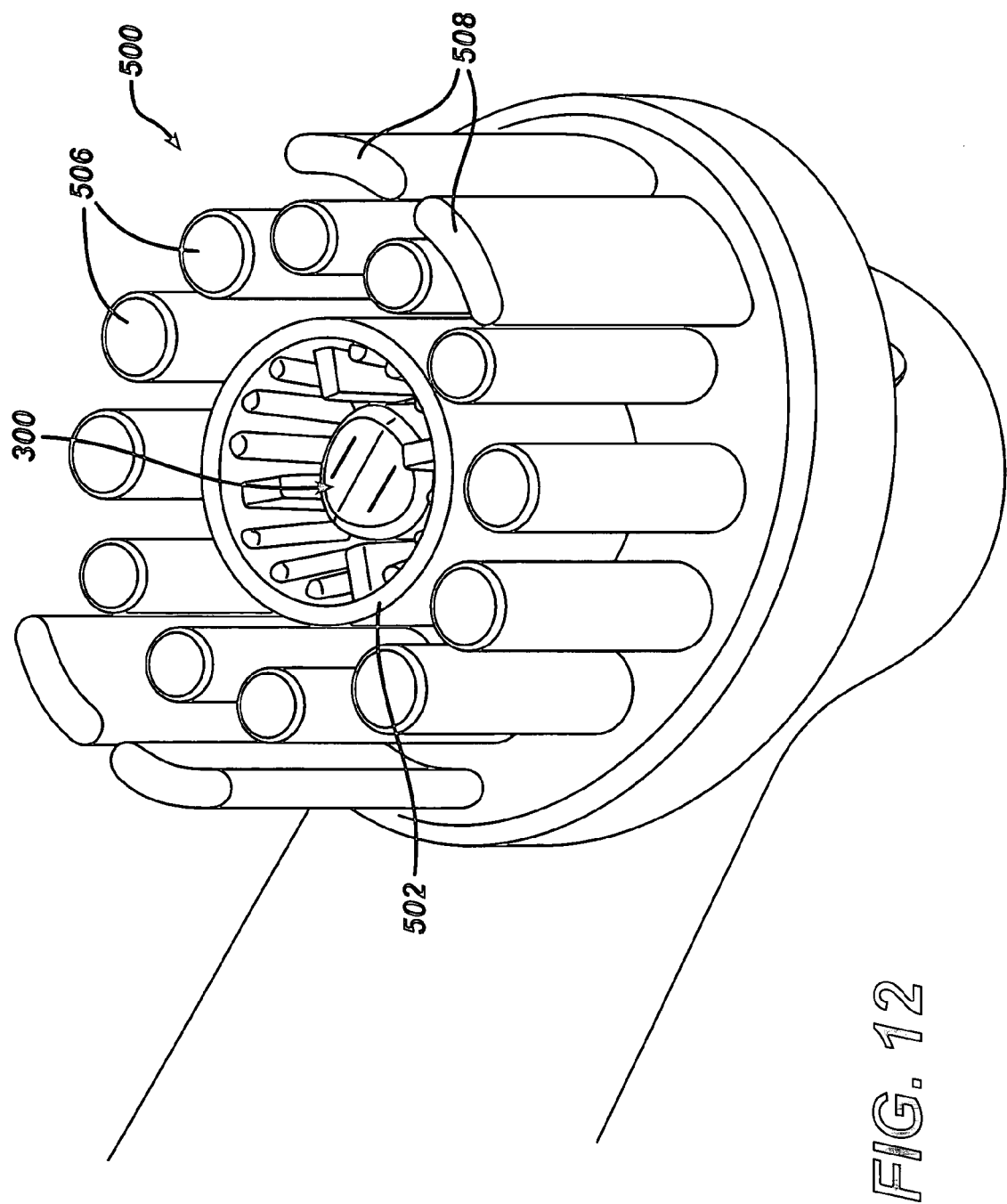
FIG. 12 is a top perspective view of an oral care device incorporating the dual valve of FIG. 6.

FIG. 12 depicts an example of the dual valve 300, depicted in FIGS. 6-8, positioned in the center of the elongated or elliptical head 500 of an electric toothbrush. The dual valve 300 is positioned inside of a prophy cup 502 made of an elastomeric material. The prophy cup 502 can provide a means of keeping the dentifrice that is dispensed from the dual valve in contact with the teeth of the user. Surrounding the prophy cup are tufts of bristles 506,508, which clean the tooth of the user.

Two passageways, through which two streams of dentifrice flow, pass through the body of the oral care device into the dual valve positioned in fluid communication with the passageways. The dentifrice then passes through the dual valve, which allows the components of the dentifrice in each of the two passageways to remain separate until they pass through the slit valves of the dual valve. Upon exiting the valve, the two components mix together inside of the prophy cup.

Examples of suitable dentifrices include those described in U.S. patent application Ser. No. 10/871,659, filed Jun. 18, 2004, titled "Oral Care Compositions," the entire contents of which is hereby incorporated by reference. In general, the dentifrices have a shear slope of at least about 1 and at most about 85. The dentifrices generally have a yield point at least about 5 Pa.

When used in an oral care device, the valves are generally at least about 0.05 inches tall and at most about 0.6 inches tall, for example, about 0.120 inches tall, and have a cross-sectional dimension of at least about 0.210×0.150 inches. In some embodiments, the valve can be about 0.170 inches in diameter (flange) by approximately 0.250 inches high above the bottom of the flange. Each lumen generally has a cross section area of at least about 0.0003 square inches, for example about 0.0007 square inches, or a minimum equivalent flow to a circular passageway with a diameter of approximately 0.030 inches. The slit length of the valves depend on a variety of factors including material durometer and elastic properties, and desired flow rates. In some embodiments, a valve material has a material hardness of at least about 45 shore A durometer and at most about 90 shore A durometer, for example about 50 shore A durometer, a flow rate of 4 ml/min, the slit length should be at least 0.040 inches.

Figure 13:
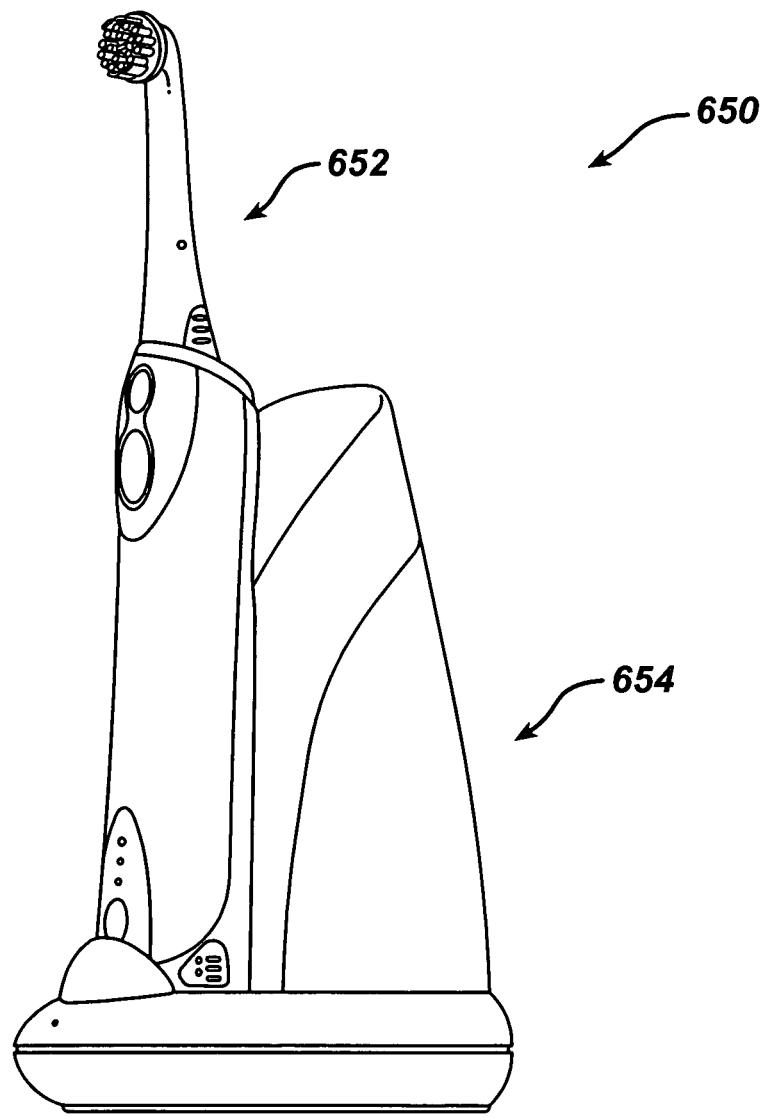
FIG. 13 is a side perspective view of an embodiment of an oral care system.

Referring to FIG. 13, an embodiment of an oral care system 650 is shown that includes an oral care device 652, in this case a toothbrush, and a docking station 654 that holds the oral care device 652 in an upright position within a receiving portion of the docking station. Oral care device 652 is a power toothbrush having a motorized head and is designed to discharge a fluid, such as a dentifrice or mouthwash or a combination of various fluids, during the brushing cycle. The docking station 654 is designed to recharge batteries that are located within the oral care device, and in some embodiments, to store fluids to refill the oral care device with the fluid(s).

In use, the dentifrice flows through the passageways by way of a pumping system in the toothbrush. The pump can be a manual pump or an electric pump, and generally exerts a pressure of up to about 50 psi on the dentifrice to deliver the fluid through the dual valve onto the tooth of the user.

Figure 14:
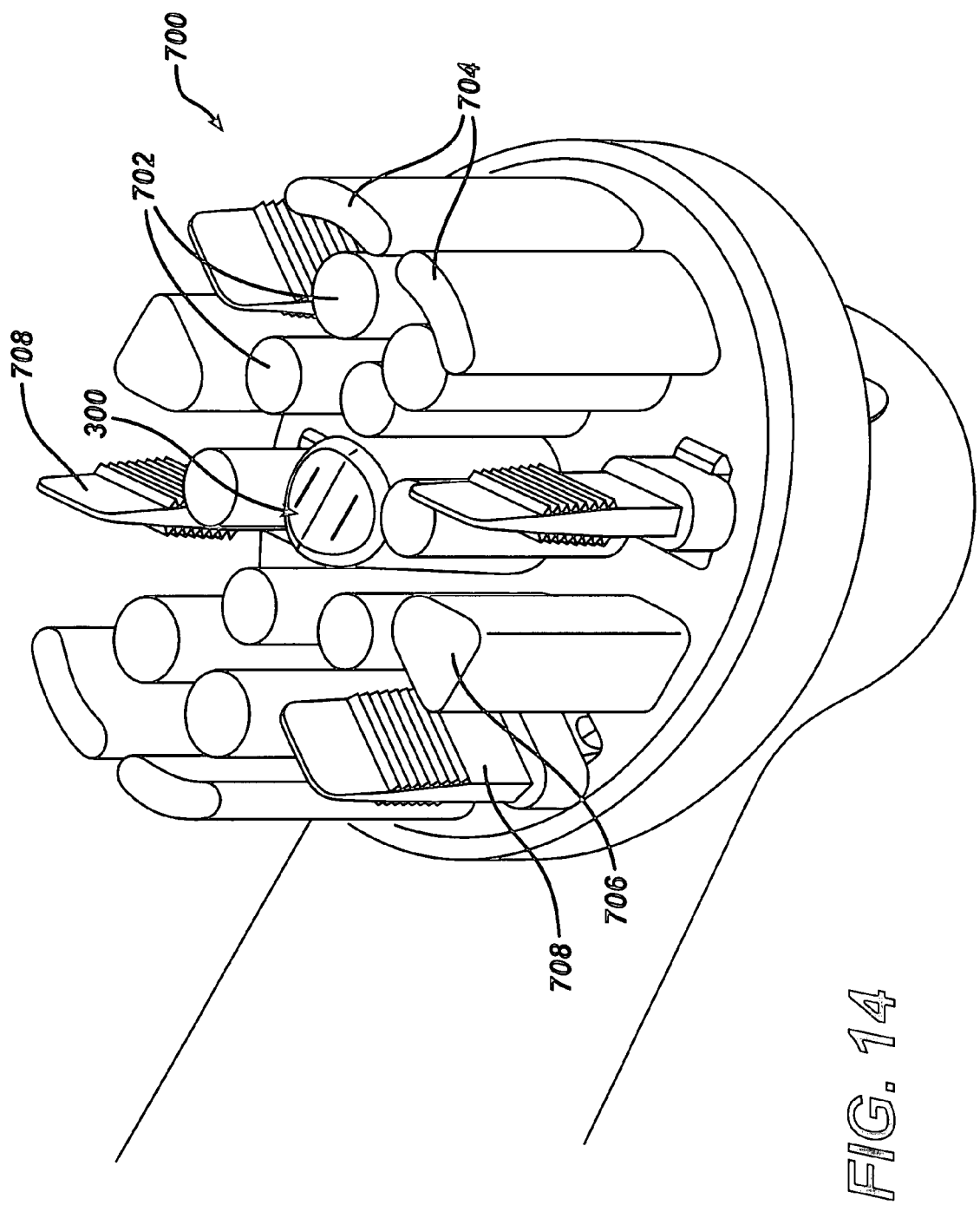
FIG. 14 is a top perspective view of another oral care device incorporating the dual valve of FIG. 6.

FIG. 14 shows an alternative embodiment of an electric toothbrush head 700 having a dual valve 300 as depicted in FIGS. 6-8. The dentifrice is delivered through the passageways in the body of the toothbrush, through the dual valve, and to the mouth of the user through the slits at the distal end of the valve. The valve is centered on the circular head of the toothbrush and surrounded by cleaning elements, e.g., tufts of bristles 702,704,706 and fins 708, which are used to clean the teeth of the user.

Figure 15:
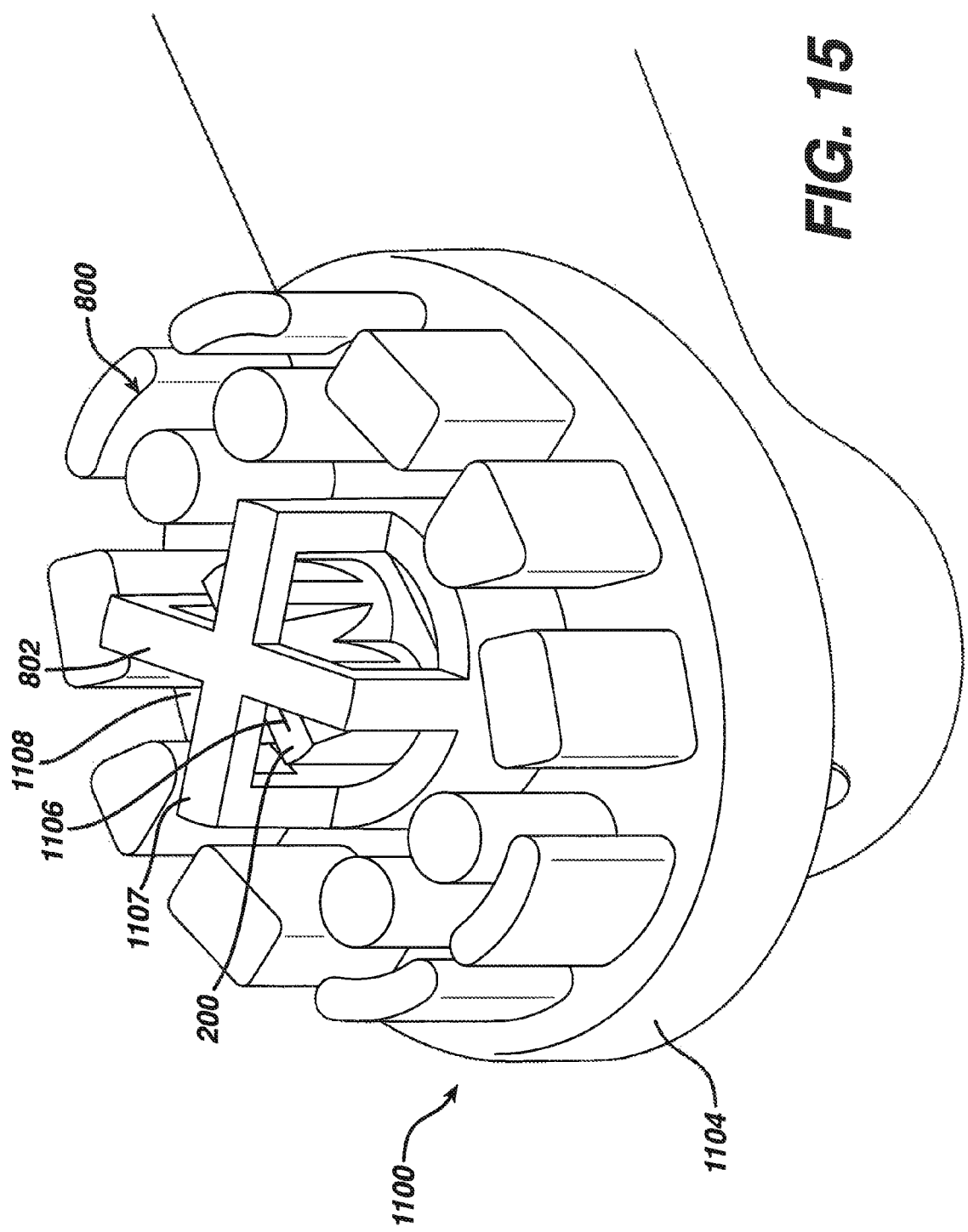
FIG. 15 is a top perspective view of an oral care device incorporating the dual duckbill valve of FIG. 5 with the cleaning elements omitted for clarity. A mixing member is positioned on the head of the oral care device.

The dual valve 200 of FIG. 5 is depicted on the head 1104 of a toothbrush head 800 in FIG. 15. The oval shaped head includes the dual valve 200 positioned approximately in the center of the oval head. The non-moving dual valve 200 is covered by a mixing member 802, which extends over the body of the dual valve, leaving exposed a portion of the slits of the dual valve. Upon exiting the dual valve, the components of the dentifrice are mixed by the mixing member, which rotates with the head when the toothbrush is in use. The dual valve is generally surrounded by cleaning elements (not shown) such as bristles and/or fins.

Figure 16:
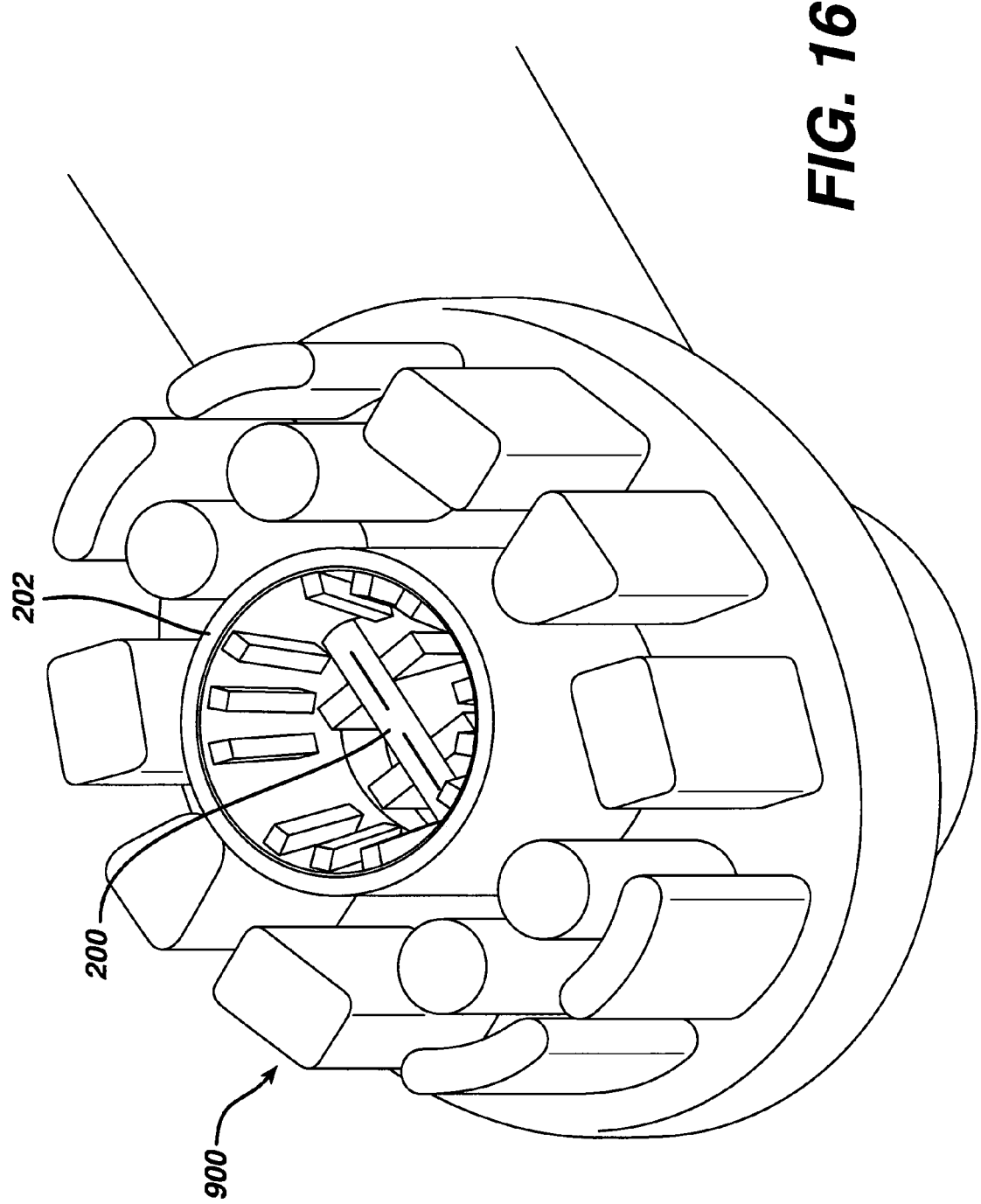
FIG. 16 is a top perspective view of an oral care device incorporating the dual duckbill valve of FIG. 5 with the cleaning elements omitted for clarity.

FIG. 16 depicts an alternative embodiment of a toothbrush head 900 that includes the dual valve 200 of FIG. 5. The non-moving dual valve 200 is positioned approximately in the center of the head and is surrounded by a prophy cup 202. The prophy cup 202 captures the dentifrice and allows mixing of the components passing through the two lumens. Moreover, the prophy cup helps to maintain the dentifrice in contact with the tooth of the user. The prophy cup is generally surrounded by cleaning elements (not shown) such as bristles and/or fins.

In general, the dual valve is made from an elastomeric material. Examples of suitable materials include but are not limited to nitrile, silicone, fluorosilicone, liquid silicone rubber, liquid fluorosilicone rubber, fluorocarbon, ethylene propylene, and thermoplastic elastomer.

The head of the oral care device can move in any desired manner. For example, the head of the oral care device can oscillate, rotate, or move in a "sonic" motion, e.g., as described in U.S. Pat. No. 5,189,751, titled "Vibrating Toothbrush Using Magnetic Driver" to Giuliani et al., the full disclosure of which is incorporated herein by reference.

In general, the head of the toothbrush can be of any shape that is configured to fit into the mouth of a user, such as a human or other mammal. Examples of preferred shapes include circular, ovular, and rectangular. The top surface area of the head is generally at least about 0.210 and at most about 0.640 square inches.

Razors

Figure 17:
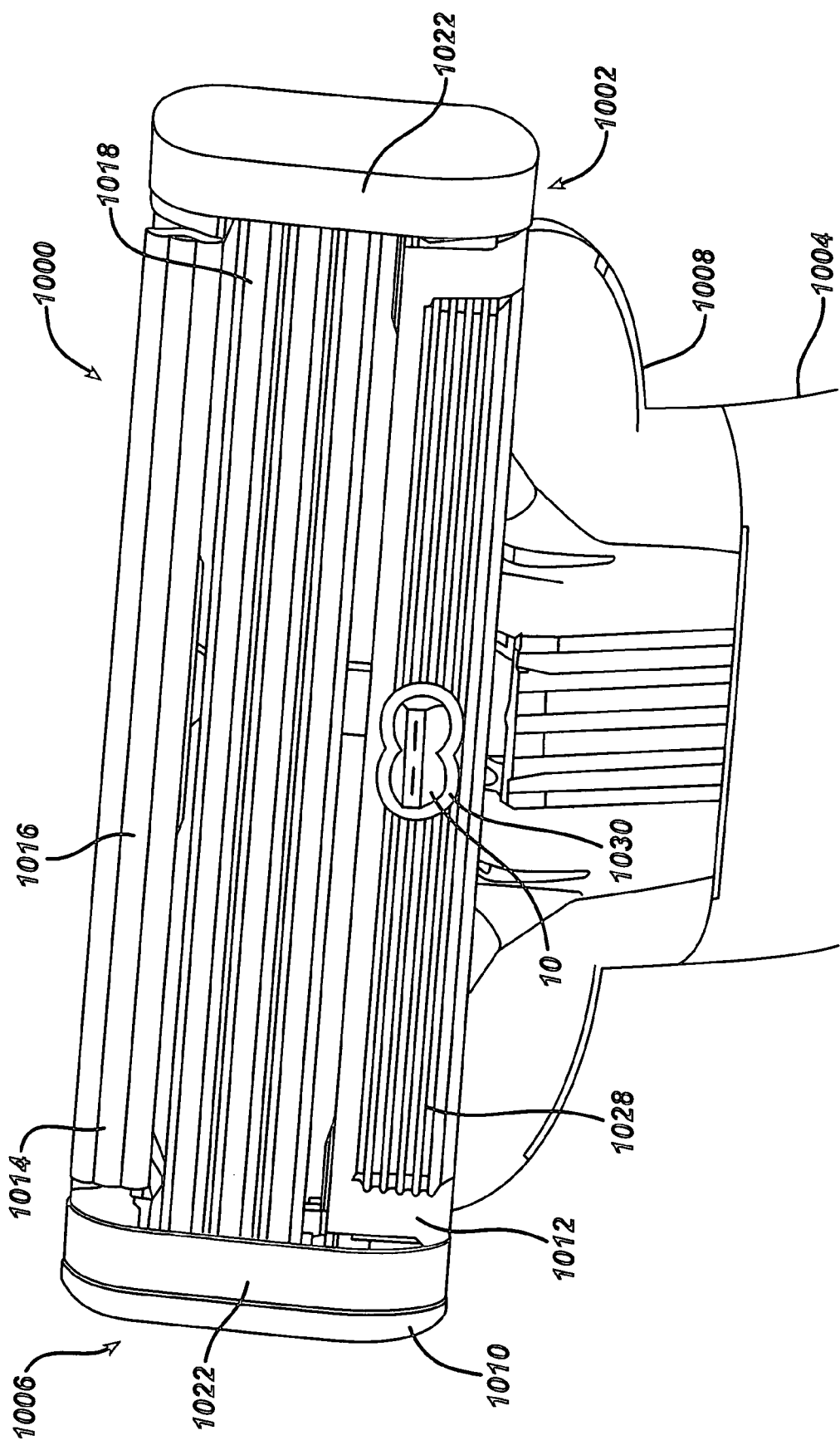
FIG. 17 is a front perspective view of a razor.

Referring to FIG. 17 shaving razor 1000 includes disposable cartridge 1002 and handle 1004. Cartridge 1002 includes a connecting member 1008, which connects cartridge 1002 to handle 1004, and a blade unit 1006, which is pivotally connected to connecting member 1008. The blade unit 1006 includes housing 1010, guard 1012 at the front of housing 1010, cap 1014 with lubricating strip 1016 at the rear of housing 1010, and three blades 1018 between guard 1012 and cap 1014.

Housing 1010 of blade unit 1006 has inwardly facing slots (not shown) in side walls 1022 for receiving ends of blade supports. Housing 1010 also has respective pairs of resilient arms (not shown), extending from the side walls 1022, on which each blade 1018 is resiliently supported. Blades 1018 are located in a relatively unobstructed region between the side walls 1022, e.g., to provide for ease of rinsing of the cartridge during use.

Guard 1012 includes elastomeric fins 1028 disposed along its length. Also disposed on guard 1012 is dual valve 10 (See FIG. 1). Similar to the construction of the oral care devices depicted in FIGS. 10A-B and 11A-B, dual valve 10 extends through the guard and is connected with associated fluid passageways (not shown) that extend through handle 1004 of the razor 1000.

Cap 1014 provides a lubricious shaving aid and is received at the rear of housing 1010. Cap 1014 may be made of a material comprising a mixture of a hydrophobic material and a water leachable hydrophilic polymer material, as is known in the art and described, e.g., in U.S. Pat. Nos. 5,113,585 and 5,454,164, the entire contents of each of which are hereby incorporated by reference.

In embodiments where the valve is attached to the handle, the cartridge sample has an opening 1030 through which the valve fits. The opening 1030 is generally large enough to allow the cartridge to pivot without causing the valve to bend to the point where the passageway shuts off.

In some embodiments, the valve is attached to the cartridge. These embodiments also include a means for fluidically connecting the passageways in the handle and cartridge. The fluid connections generally allow sufficient room for the cartridge to pivot, or themselves bend to accommodate pivoting. Because of the additional complexity, in some embodiments, it is preferable for the valve to be attached to the handle.

Mixing members

Referring to FIG. 15, a mixing member 802 is positioned on the head 800 of an oral care device 1100. Mixing member 802 is positioned over an outlet 1106 in valve 200 through which fluid, such as dentifrice, flows, and includes shearing members 1107 positioned above outlet 1106. Mixing member 802 and outlet 1106 rotate relative to each other to create shear forces in the fluid as it exits outlet 1106. For example, one of the mixing member 802 or outlet 1106 can be stationary while the other rotates. Or alternatively, both mixing member 802 and outlet 1106 can rotate, for example in opposite directions. Mixing member 802 includes openings 1108 through which the fluid can pass to reach the teeth of a user.

Figure 18:
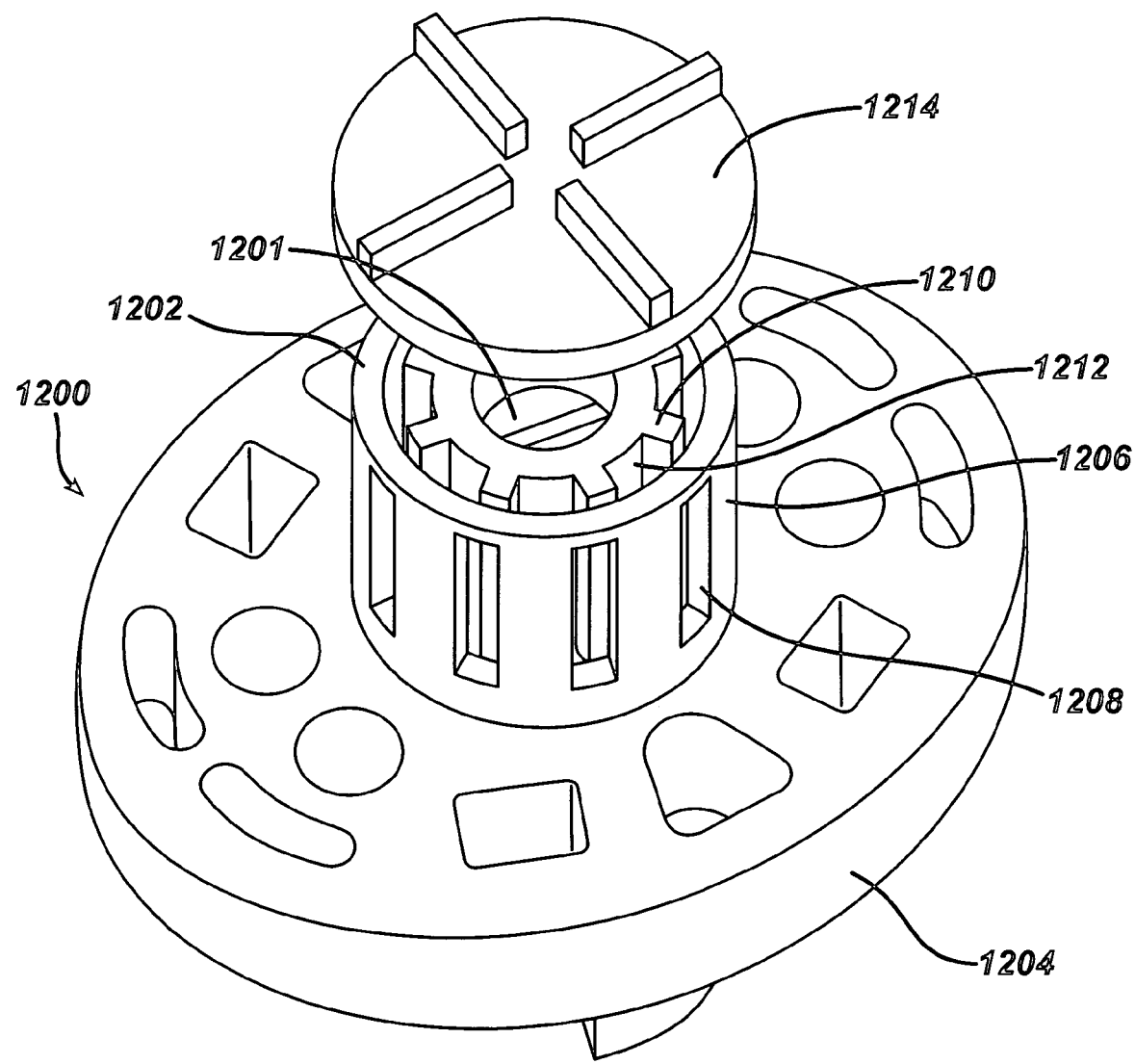
FIG. 18 is a top perspective of an oral care device including a head, with a valve and a mixing member positioned on the head.

An alternative embodiment of a mixing member is depicted in FIG. 18. Referring to FIG. 18, mixing member 1202 is positioned in the center of a head 1204 of an oral care device 1200 and surrounding a valve 1201. Mixing member 1202 includes a first cylindrical member 1206 having a plurality of slots 1208 that extend substantially the entire length of cylindrical member 1206. A second cylindrical member 1210 having a plurality of grooves 1212 is sized and shaped to fit inside first cylindrical member 1206. Fluid passes between first and second cylindrical members 1206 and 1210, which rotate relative to each other to create shear forces in the fluid. A cap 1214 is positioned on top of the first and second cylindrical members to force the fluid to exit the mixing member in a radial direction.

Figure 19:
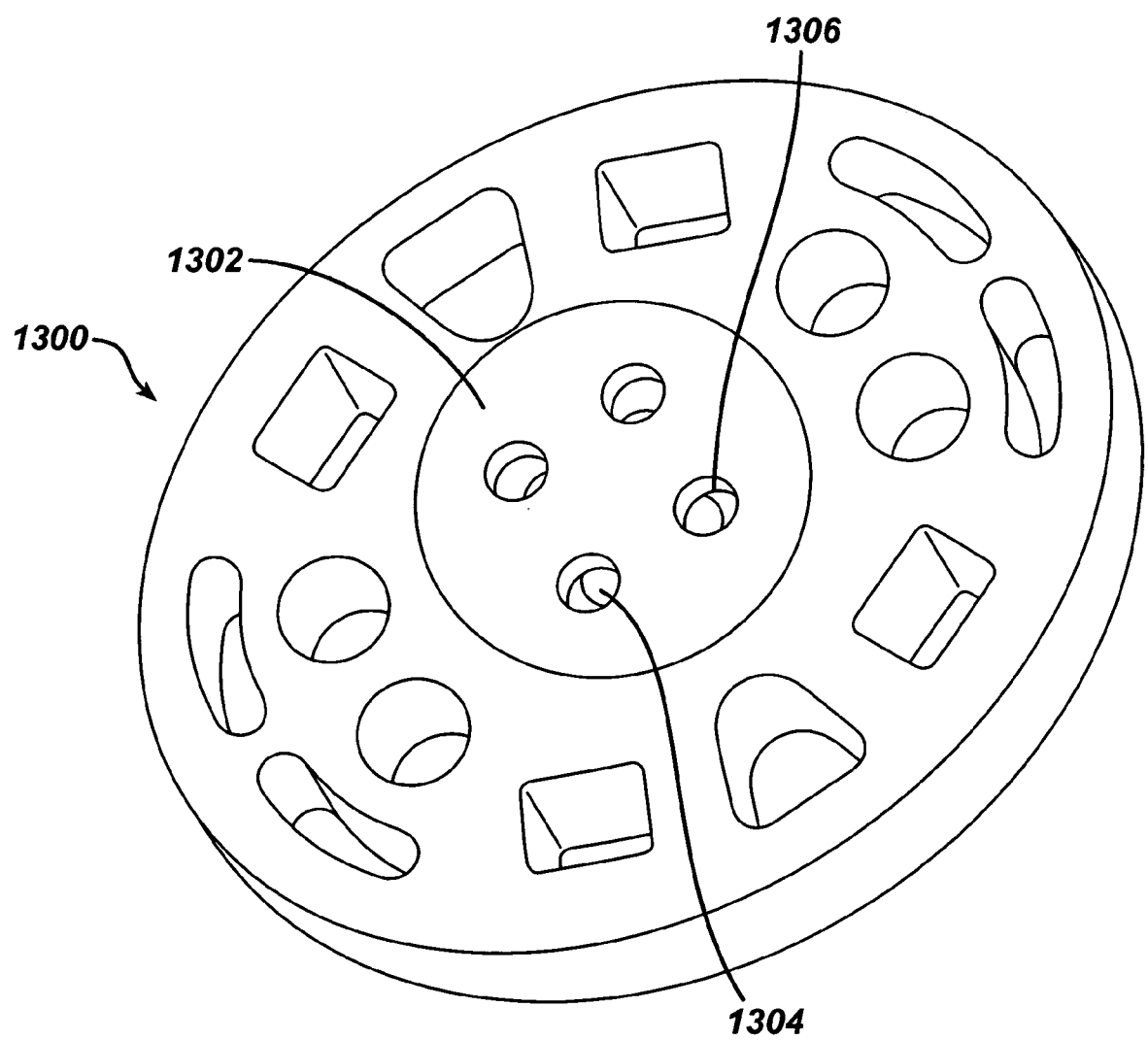
FIG. 19 is a top perspective of an oral care device having a mixing member positioned on the head.

Referring to FIG. 19, another embodiment of a mixing member includes a circular member 1302 positioned over a plurality of outlets 1304 through which fluid passes from the head 1300 of an oral care device (not shown). Circular member 1302 has a plurality of openings 1306, which engage the fluid as it passes through outlets 1304. Shear forces are created by motion of circular member 1302 to outlets 1304, e.g., rotation of the circular member 1302, thereby mixing the fluid as it passes through the circular openings 1306 in mixing member 1302.

While the mixing members have been shown on oral care devices, the mixing members can also be incorporated into a razor. For example a mixing member from one of FIGS. 15, 18, or 19 can be positioned over a valve on a razor such as the razor depicted in FIG. 17.

A number of embodiments of the invention have been described. Nevertheless, it will be understood that various modifications may be made without departing from the spirit and scope of the invention. Accordingly, other embodiments are within the scope of the following claims.

What is claimed is:

1. An oral care device, the device comprising:
   a body, constructed to be held by a user, including two or more passageways through which fluids can flow, and
   a head, extending from the body and being sized to fit in a user's mouth and comprising a plurality of tooth-cleaning elements; and
   a valve body positioned on the head, wherein the valve body comprises an upper portion and a base, wherein the upper portion defines a plurality of lumens, each lumen terminating in a valve having an exit; and
   a mixing member disposed above the valves and wherein the mixing member and the valves move relative to each other to create a shear force in the fluid that exits the valves.

2. The oral care device of claim 1, wherein the plurality of tooth cleaning elements comprise a plurality of bristles extending from said head.

3. The oral care device of claim 1, further comprising reservoirs, in communication with the passageways, configured to contain a supply of the fluid.

4. The oral care device of claim 3, wherein the reservoirs are disposed within the body.

5. The device of claim 1, wherein the valve body comprises tapered lumens.

6. The device of claim 1, wherein each valve is a slit valve.

7. The device of claim 1, wherein each valve is a duckbill valve.

8. The device of claim 1, wherein the base forms a seal with an outlet of the head.

9. The device of claim 1, wherein the valve body has a height of between about 0.100 inches and about 0.500 inches.

10. The device of claim 1, wherein the valve body comprises an elastomer.

11. The device of claim 1, wherein the valve body dispenses media at a rate of between about 0.2 ml/minute and about 6.0 ml/minute.

12. The device of claim 1, wherein the device is a toothbrush.

13. The device of claim 12, wherein the device is a power toothbrush.

14. The device of claim 1, wherein the valve body is disposed in the center of the head.

15. The device of claim 1, wherein at least one of the fluids comprises a dentifrice.

16. The device of claim 1, wherein the valve body is disposed in the center of the head and the plurality of bristles are disposed surrounding the valve body.

17. The device of claim 1, wherein the head oscillates.

18. The device of claim 1, wherein the mixing member further comprises a shearing member.

19. The device of claim 1, wherein the plurality of lumens including a first lumen and a second lumen.

20. The device of claim 19, wherein the first lumen dispenses a first media and the second lumen dispenses a second media, which is different from the first media.

* * * * *